(12) United States Patent
Schoentjes et al.

(10) Patent No.: US 8,703,973 B2
(45) Date of Patent: Apr. 22, 2014

(54) BENZOCYCLOHEPTANE AND BENZOXEPINE DERIVATIVES

(75) Inventors: Bruno Schoentjes, Brussels (BE); Alain Philippe Poncelet, La Manoir sur Seine (FR); Julien Georges Pierre-Olivier Doyon, Beerse (BE); Joannes Theodorus Maria Linders, Eindhoven (NL); Lieven Meerpoel, Beerse (BE); Luc August Laurentius Ver Donck, Kasterlee (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/597,293

(22) Filed: Aug. 29, 2012

(65) Prior Publication Data

US 2012/0322796 A1 Dec. 20, 2012

Related U.S. Application Data

(62) Division of application No. 12/989,684, filed as application No. PCT/EP2009/055034 on Apr. 27, 2009, now Pat. No. 8,278,466.

(30) Foreign Application Priority Data

Apr. 28, 2008 (EP) .................................. 08155261

(51) Int. Cl.
*C07D 305/00* (2006.01)
*C07C 211/00* (2006.01)

(52) U.S. Cl.
USPC .......................................... 549/207; 564/428

(58) Field of Classification Search
USPC .......................................... 549/355; 564/428
See application file for complete search history.

(56) References Cited

U.S. PATENT DOCUMENTS

| 4,091,115 A | 5/1978 | Nedelec et al. |
| 4,736,031 A | 4/1988 | Sugihara et al. |
| 6,013,809 A | 1/2000 | Zimmer et al. |

FOREIGN PATENT DOCUMENTS

| EP | 1057485 A1 | 12/2000 |
| WO | WO 2004/014412 A1 | 2/2004 |
| WO | WO 2008/143835 A1 | 11/2008 |

OTHER PUBLICATIONS

Barreiro, M.L, and Tena-Sempre, M., "At the Cutting Edge. Ghrelin and reproduction: a novel signal linking energy status and fertility?*", Molecular and Cellular Endocrinology, 2004, pp. 1-9, vol. 226.
Dembinski et al., "Ghrelin Attenuates The Development of Acute Pancreatitis in Rats.", J. of Physiology and Pharmacology, 2003, pp. 561-573, vol. 54(4).
Diano et al., "Ghrelin controls hippocampal spine synapse density and memory performance.", Nature Neuroscience, 2006, pp. 381-388, vol. 9.
Dong et al., "Ghrelin Antagonized 1-Methyl-4-Phenylpyridinium (MPP+)-Induced Apoptosis in MES23.5 Cells.", J. Mol. Neuroscience, 2009, pp. 182-189, vol. 37.
Fukushima et al., "Ghrelin Directly Regulates Bone Formation.", J. Bone and Mineral Research, 2005, pp. 790-798, vol. 20(5).
Howard et al., "A Receptor in Pituitary and Hypothalamus That Functions in Growth Hormone Release.", Science, 1996, pp. 974-977, vol. 273.
"IUPAC Tentative Rules for the Nomenclature of Organic Chemistry. Section E. Fundamental Stereochemistry.", J. Org. Chem., Sep. 1970, pp. 2849-2867, vol. 35(9).
Jiang et al., "Ghrelin antagonizes MPTP-induced neurotoxicity to the dopaminergic neurons in mouse substantia nigra.", Experimental Neurology, 2008, pp. 532-537, vol. 212.
Kojima et al, "Ghrelin is a growth-hormone-releasing acylated peptide from stomach.", Nature, Dec. 9, 1999, pp. 656-660, vol. 402.
Lago et al., "Ghrelin, the Same Peptide for Different Functions: Player or Bystander?", Vitamins and Hormones. 2005, pp. 405-432, vol. 71.

(Continued)

*Primary Examiner* — Nizal Chandrakumar

(57) ABSTRACT

The present invention relates to a compound of formula (I)

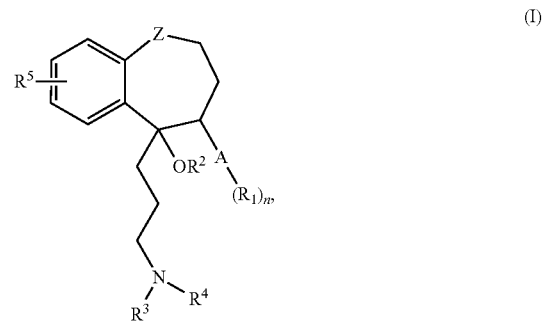

including any stereochemically isomeric form thereof, wherein the substituents are as defined in the specification and the claims; a N-oxide thereof, a pharmaceutically acceptable salt thereof or a solvate thereof;

provided that the compound is other than

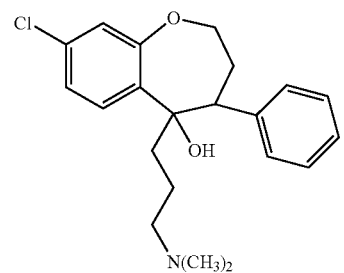

or a pharmaceutically acceptable salt thereof.
The claimed compounds are useful for the treatment of a disease, the treatment of which is affected, mediated or facilitated by activating the GHS1A-r receptor. The invention also relates to pharmaceutical compositions thereof and processes for the preparation thereof.

17 Claims, 1 Drawing Sheet

(56) References Cited

OTHER PUBLICATIONS

Li et al., "Ghrelin acts on the dorsal vagal complex to stimulate pancreatic protein secretion.", Am. J. of Physiol., 2006, pp. G1350-1358, vol. 290.

Lutter et al., "The orexigenic hormone ghrelin defends against depressive symptoms of chronic stress.", Nature Neuroscience, 2008, pp. 752-753, vol. 11(7).

Murray et al., "Ghrelin for the Gastroenterologist: History and Potential.", Gastroenterology, 2003, pp. 1492-1502, vol. 125.

Nagaya, N. and Kangawa, K., "Ghrelin improves left ventricular dysfunction and cardiac cachexia in heart failure.", Current Opinion in Pharmacology, 2003, pp. 146-151, vol. 3.

Nagaya, N. and Kangawa, K., "Ghrelin, a novel growth hormone-releasing peptide, in the treatment of chronic heart failure.", Regulatory Peptides, 2003, pp. 71-77, vol. 114.

Nakahara et al., "Effect of chronic treatments with ghrelin on milk secretion in lactating rats.", Biochemical and Biophysical Research Communications, 2003, pp. 751-755, vol. 303.

Peeters,T.L., "Central and Peripheral Mechanisms by Which Ghrelin Regulates Gut Motility.", J. of Physiology and Pharmacology, 2003, pp. 95-103, 54(Suppl.4).

Szentirmai et al., "Ghrelin microinjection into forebrain sites induces wakefulness and feeding in rats.", Am. J. Physiol., 2007,pp. R575-R585, vol. 292.

Van der Lely et al., "Biological, Physiological, Pathophysiological, and Pharmacological Aspects of Ghrelin.", Endocrine Reviews, 2004, pp. 426-457, vol. 25.

Khanna et al., "Agents acting on the central nervous system: Part VIII-5-Substituted -6,7,8,9-tetrahydro-5H-b-enzocycloheptenes.", Indian Journal of Chemstry, Jan. 1, 1967, pp. 347-352, vol. 5(1), Jodhpur, IN., XP009107043.

Protiva et al., "Benzocycloheptenes and heterocyclic analogs as potential drugs. IV. Amines derived from 4-phenyl-8-chloro-2,3,4,5-tetrahydro-1-benzoxepin.", Collection of Czechoslovak Chemical Communications, 1972, pp. 2081-2090, vol. 37(6), XP0091007038.

Protiva et al., "Benzocycloheptenes and Heterocyclic Analogues As Potential Drugs. IL* Amines of 8-chloro-2,3,4,5-tetrahydro-1-benzoxepin Series**", Collection of Czechoslovak Chemical Communications, Jan. 1, 1972, pp. 868-886, vol. 37(3), Institute of Organic Chemistry & Biochemistry, Prague, XP002097421.

International Search Report, International Application No. PCT/EP2009/055304, Date of Mailing of International Search Report, Sep. 24, 2009.

Written Opinion, relating to International Application No. PCT/EP2009/055304, Date of Mailing of Written Opinion, Sep. 24, 2009.

Arvat et al., "Growth Hormone-Releasing Hormone and Growth Hormone Secretagogue-Receptor Ligands.", Endocrine, 2001, pp. 35-43, vol. 14.

Barreiro, M.L, and Tena-Sempre, M., At the Cutting Edge. Ghrelin and reproduction: a novel signal linking energy status and fertility?"", Molecular and Cellular Endocrinology, 2004, pp. 1-9, vol. 226.

Bowers, C.Y., "Growth hormone releasing peptides: physiology and clinical applications.", Curr. Opin. Endocrinol. Diabetes, 2000, pp. 168-174, vol. 7.

Carlini et al., "Ghrelin increases anxiety-like behavior and memory retention in rats.", Biochemical and Biophysical Research Communications, 2002, pp. 739-743, vol. 299.

Cianfarani et al., "Hormonal Regulation of Postnatal Growth in Children Born Small for Gestational Age.", Hormone Research, 2006, pp. 70-74, vol. 65(Supp.3).

Cross, "Rules for the Nomenclature of Organic Chemistry. Section E: Stereochemistry (Recommendations 1974).", *Pure Appl. Chem.*, 1976, pp. 11-30.

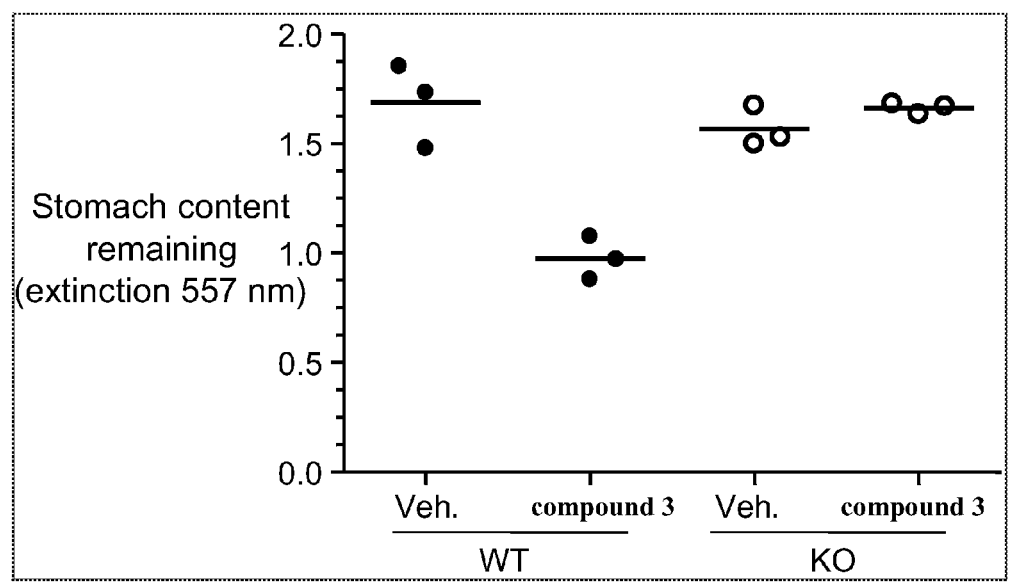

BENZOCYCLOHEPTANE AND BENZOXEPINE DERIVATIVES

CROSS REFERENCE TO RELATED APPLICATIONS

This application is a divisional of U.S. application Ser. No. 12/989,684, filed Oct. 26, 2010, the disclosure of which is hereby incorporated by reference in its entirety, which is the U.S. national stage of Application No. PCT/EP2009/055034, filed Apr. 27, 2009, which application claims priority from EP 08155261.4, filed Apr. 28, 2008.

FIELD OF THE INVENTION

The present invention concerns benzocycloheptane and benzoxepine derivatives having ghrelin receptor modulating activity, in particular ghrelin receptor agonistic properties (GHS1A-r agonistic properties). The invention further relates to methods for their preparation and pharmaceutical compositions comprising them. The invention also relates to the use of said compounds for the manufacture of a medicament for the prevention or the treatment of a disease by activating the ghrelin receptor.

DESCRIPTION OF THE FIGURE

FIG. 1 describes the gastric content (measured as extinction units of phenol red) remaining 15 minutes after administration of a phenol red containing test meal by oral gavage in GHS1A-r$^{+/+}$ (WT) and GHS1A-r$^{-/-}$ (KO) mice pretreated with saline (Vehicle) or compound 3 (10 mg/kg SC) 30 minutes before the meal (individual data and mean, n=3).

DESCRIPTION OF BACKGROUND ART

Protiva et al., Collection of Czechoslovak Chemical Communications, 37(6), 1972, 2081-2090, relates to benzocycloheptenes and heterocyclic analogues as potential drugs. It is disclosed that the pharmacodynamic effects of the compounds are weak. Protiva et al., Collection of Czechoslovak Chemical Communications, 37(3), 1972, 868-886, relates to benzocycloheptenes and heterocyclic analogues as potential drugs. It is disclosed that even if a number of the compounds described possessed indications of interesting activities, the experimental findings did not justify in any single case further detailed pharmacological or toxicological studies.

U.S. Pat. No. 6,013,809 describes substituted heterocyclic benzocycloalkenes and the use thereof as substances having an analgesic effect.

DESCRIPTION OF THE INVENTION

The compounds of the invention differ from the prior art compounds in structure, in their pharmacological activity and/or pharmacological potency.

One aspect of the present invention relates to a compound of formula

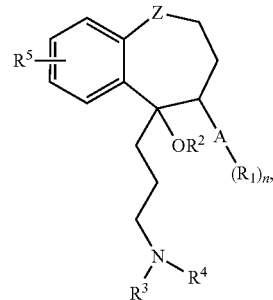

(I)

including any stereochemically isomeric form thereof, wherein

A represents phenyl, thienyl, furanyl or a 6-membered aromatic heterocycle containing 1 or 2 nitrogen atoms; wherein said phenyl, thienyl, furanyl or 6-membered aromatic heterocycle may optionally be fused with phenyl or a 6-membered aromatic heterocycle containing 1 or 2 nitrogen atoms;

Z represents $CH_2$ or O;

$R^1$ represents halo, hydroxyl, $C_{1-4}$alkyl, $C_{1-4}$alkyloxy, polyhalo$C_{1-4}$alkyl, cyano, nitro, amino, mono or di($C_{1-4}$alkyl)amino; or in case A represents phenyl then two adjacent $R^1$ substituents may be taken together to form a radical of formula —O—$CH_2$—O— (a-1); or —O—$CH_2$—$CH_2$—O— (a-2);

$R^2$ represents hydrogen or $C_{1-4}$alkyl;

$R^3$ and $R^4$ each independently represent hydrogen, $C_{1-6}$alkyl, $C_{1-4}$alkyloxy$C_{1-6}$alkyl or phenyl$C_{1-4}$alkyl; or $R^3$ and $R^4$ are taken together with the nitrogen to which they are attached to form a radical of formula (b-1) or (b-2)

(b-1)

or

(b-2)

with $X_1$ representing $CH_2$ or CHOH; and $X_2$ representing $CH_2$, O or $NR^6$;

$R^5$ represents hydrogen, halo, $C_{1-4}$alkyl, $C_{1-4}$alkyloxy or trifluoromethyl;

$R^6$ represents hydrogen, $C_{1-4}$alkyl, $C_{1-4}$alkylcarbonyl, $C_{1-4}$alkyloxycarbonyl, phenyloxycarbonyl;

n represents an integer of value 0, 1, 2, 3, 4 or 5;

a N-oxide thereof, a pharmaceutically acceptable salt thereof or a solvate thereof;

provided that the compound is other than

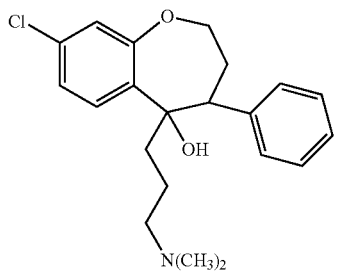 [SMILES: CN(C)CCCC1(O)c2ccc(Cl)cc2OCCC1c1ccccc1]

or a pharmaceutically acceptable salt thereof.

The present invention also relates to the use of a compound of formula (I) for the manufacture of a medicament for preventing or treating a disease by activating the ghrelin receptor, in particular for treating a disease by activating the ghrelin receptor.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like.

The term halo is generic to fluoro, chloro, bromo and iodo. As used hereinbefore or hereinafter, polyhalo$C_{1-4}$alkyl as a group or part of a group is defined as mono- or polyhalosubstituted $C_{1-4}$alkyl, for example methyl substituted with one or more fluoro atoms, for example, difluoromethyl or trifluoromethyl, 1,1-difluoro-ethyl or 1,1-difluoro-2,2,2-trifluoroethyl and the like. In case more than one halogen atoms are attached to a $C_{1-4}$alkyl group within the definition of polyhalo$C_{1-4}$alkyl, they may be the same or different.

When any variable occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of formula (I) are able to form by reaction between a basic nitrogen of a compound of formula (I) and an appropriate quaternizing agent, such as, for example, an optionally substituted $C_{1-6}$alkylhalide, arylhalide, $C_{1-6}$alkylcarbonylhalide, arylcarbonylhalide, or aryl$C_{1-6}$alkylhalide, e.g. methyliodide or benzyliodide, wherein aryl represents unsubstituted or substituted phenyl. Other reactants with good leaving groups may also be used, such as for example $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. The counterion of choice can be introduced using ion exchange resins.

Preferably, the term salt means the pharmaceutically acceptable acid addition salt forms and the pharmaceutically acceptable metal or amine addition salt forms.

The N-oxide forms of the present compounds are meant to comprise the compounds of formula (I) wherein one or several tertiary nitrogen atoms are oxidized to the so-called N-oxide.

The term solvate comprises the hydrates and solvent addition forms which the compounds of formula (I) are able to form, as well as the salts thereof. Examples of such forms are e.g. hydrates, alcoholates and the like.

It will be appreciated that some of the compounds of formula (I) and their N-oxides, salts, and solvates may contain one or more centers of chirality and exist as stereochemically isomeric forms.

The term "stereochemically isomeric forms" as used hereinbefore or hereinafter defines all the possible stereoisomeric forms which the compounds of formula (I), and their N-oxides, salts or solvates may possess. Unless otherwise mentioned or indicated, the chemical designation of compounds denotes the mixture of all possible stereochemically isomeric forms, as well as each of the individual isomeric forms of formula (I) and their N-oxides, salts or solvates, substantially free, i.e. associated with less than 10%, preferably less than 5%, in particular less than 2% and most preferably less than 1% of the other isomers. Thus, when a compound of formula (I) is for instance specified as cis, this means that the compound is substantially free of the trans isomer. Or if a compound of formula (I) is for instance specified as cis (+), this means that the compound is substantially free of the cis(−) isomer.

From formula (I) it is evident that the compounds of this invention have at least two asymmetric carbon atoms in their structures, namely the carbon atom carrying the —OR$^2$ and —CH$_2$CH$_2$CH$_2$—NR$^3$R$^4$ substituent and the carbon atom carrying the -A-(R$^1$)$_n$ substituent. In the structure below, these asymmetric carbon atoms are indicated with *1 and *2.

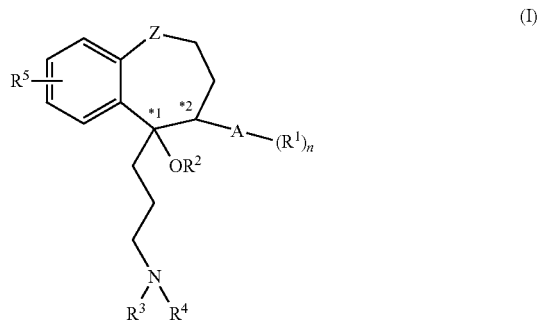

Depending on the nature of the substituents R$^1$ to R$^5$, the compounds of formula (I) may contain a third or further asymmetric carbon atoms. Consequently the compounds of formula (I) can exist under different stereochemically isomeric forms. Unless otherwise mentioned or indicated, the chemical designation of compounds denotes the mixture of all possible stereochemically isomeric forms, said mixtures containing all diastereoisomers and enantiomers of the basic molecular structure.

The absolute configuration of each asymmetric center may be indicated by the stereochemical descriptors R and S, this R and S notation corresponding to the rules described in Pure Appl. Chem. 1976, 45, 11-30 and well-known to the skilled person. Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where the first R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The terms cis and trans are used herein in accordance with Chemical Abstracts nomenclature (J. Org. Chem. 1970, 35 (9), 2849-2867), and refer to the position of the substituents on a ring moiety, more in particular on the cycloheptane or oxepine ring in the compounds of formula (I). For instance, when establishing the cis or trans configuration of the cycloheptane or oxepine ring, the substituent with the highest priority on the carbon atom *1 of the cycloheptane or oxepine ring, and the substituent with the highest priority on the carbon atom *2 of the cycloheptane or oxepine ring are considered (the priority of a substituent being determined according to the Cahn-Ingold-Prelog sequence rules). When said two substituents with highest priority are at the same side of the ring then the configuration is designated cis, if not, the configuration is designated trans.

It is evident that the cis and trans racemates may be further resolved into their optical isomers, cis(+) and cis(−), respectively trans(+) and trans(−) by the application of art-known methodologies. In case additional asymmetric centra are present in the abovementioned compounds, the resulting mixtures of stereoisomers may be further separated by art-known methodologies further described hereinafter. Preferably, if a specific stereochemical form is desired, said compound can be synthesized by stereoselective methods of preparation, which advantageously employ enantiomerically pure starting materials.

Since the stereochemical configuration (cis or trans) may already be fixed in intermediates of formula (II) by their synthesis protocol, it is already possible to separate cis and trans forms at that stage of the preparation. Intermediates of formula (II) have preferably a cis configuration. Compounds of formula (I) derived from the cis intermediates of formula (II) also have the cis configuration. Compounds of formula (I) have preferably a cis configuration.

Stereochemically isomeric forms of the compounds of formula (I) are obviously intended to be embraced within the scope of this invention.

The compounds of (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Some of the compounds of formula (I) may also exist in their tautomeric form. Such forms although not explicitly indicated in the above formula (I) are intended to be included within the scope of the present invention.

Whenever used hereinafter, the term "compounds of formula (I)" or any subgroup thereof, is meant to also include their N-oxide forms, their salts, their stereochemically isomeric forms and their solvates. Of special interest are those compounds of formula (I) which are stereochemically pure.

Whenever used hereinbefore or hereinafter that substituents can be selected each independently out of a list of numerous definitions, all possible combinations are intended which are chemically possible.

An interesting embodiment of the present invention are those compounds of formula (I) wherein A represents phenyl or phenyl substituted with 1 to 5 $R^1$ substituents, in particular 1 to 3 $R^1$ substituents, more in particular 1 or 2 $R^1$ substituents.

An interesting embodiment of the present invention are those compounds of formula (I) wherein A represents

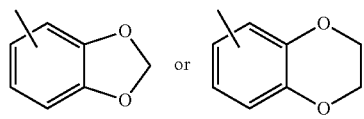

An interesting embodiment of the present invention are those compounds of formula (I) wherein A represents a 6-membered aromatic heterocycle containing 1 or 2 nitrogen atoms or A represents a 6-membered aromatic heterocycle containing 1 or 2 nitrogen atoms substituted with 1 to 5 $R^1$ substituents, in particular 1 to 3 $R^1$ substituents, more in particular 1 or 2 $R^1$ substituents; in particular A represents pyridyl or pyrimidinyl, each of said pyridyl or pyrimidinyl optionally being substituted with 1 to 5 $R^1$ substituents, in particular 1 to 3 $R^1$ substituents, more in particular 1 or 2 $R^1$ substituents.

An interesting embodiment of the present invention are those compounds of formula (I) wherein A represents a 6-membered aromatic heterocycle containing 1 or 2 nitrogen atoms; wherein said heterocycle is fused with phenyl; said bicycle optionally being substituted with 1 to 5 $R^1$ substituents, in particular 1 to 3 $R^1$ substituents, more in particular 1 or 2 $R^1$ substituents; in particular A represents quinolinyl or quinolinyl substituted with 1 to 5 $R^1$ substituents, in particular 1 to 3 $R^1$ substituents, more in particular 1 or 2 $R^1$ substituents.

An interesting embodiment of the present invention are those compounds of formula (I) wherein A represents thienyl or furanyl.

An interesting embodiment of the present invention are those compounds of formula (I) wherein A represents thienyl or furanyl, each substituted with 1 or 2 $R^1$ substituents.

An interesting embodiment of the present invention are those compounds of formula (I) or, whenever possible, any subgroup thereof as mentioned hereinbefore or hereinafter as interesting embodiment, wherein Z represents $CH_2$.

An interesting embodiment of the present invention are those compounds of formula (I) or, whenever possible, any subgroup thereof as mentioned hereinbefore or hereinafter as interesting embodiment, wherein Z represents O.

An interesting embodiment of the present invention are those compounds of formula (I) or, whenever possible, any subgroup thereof as mentioned hereinbefore or hereinafter as interesting embodiment, wherein $R^1$ represents halo, hydroxyl, $C_{1-4}$alkyl or $C_{1-4}$alkyloxy.

An interesting embodiment of the present invention are those compounds of formula (I) or, whenever possible, any subgroup thereof as mentioned hereinbefore or hereinafter as interesting embodiment, wherein $R^2$ represents hydrogen.

An interesting embodiment of the present invention are those compounds of formula (I) or, whenever possible, any subgroup thereof as mentioned hereinbefore or hereinafter as interesting embodiment, wherein $R^2$ represents $C_{1-4}$alkyl, in particular methyl.

An interesting embodiment of the present invention are those compounds of formula (I) or, whenever possible, any subgroup thereof as mentioned hereinbefore or hereinafter as interesting embodiment, wherein $R^3$ and $R^4$ each independently represent hydrogen, $C_{1-6}$alkyl, $C_{1-4}$alkyloxy$C_{1-6}$alkyl, or phenyl$C_{1-4}$alkyl; or $R^3$ and $R^4$ are taken together with the nitrogen to which they are attached to form a radical of formula (b-1) or (b-2)

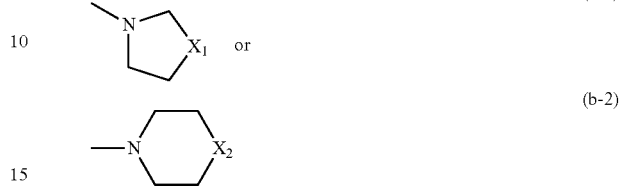

with $X_1$ representing $CH_2$ or CHOH; and $X_2$ representing $CH_2$, O or NH; in particular $R^3$ and $R^4$ each independently represent hydrogen, $C_{1-6}$alkyl, $C_{1-4}$alkyloxy$C_{1-6}$alkyl, or phenyl$C_{1-4}$alkyl; or $R^3$ and $R^4$ are taken together with the nitrogen to which they are attached to form a radical of formula (b-1) or (b-2)

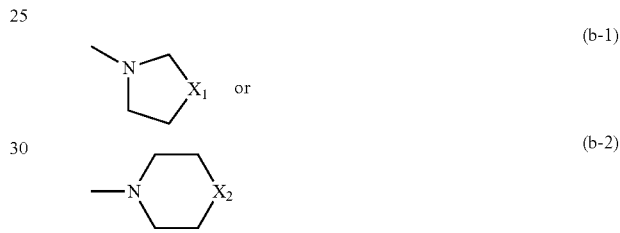

with $X_1$ representing $CH_2$ or CHOH; and $X_2$ representing $CH_2$; more in particular $R^3$ and $R^4$ each independently represent hydrogen, $C_{1-6}$alkyl, $C_{1-4}$alkyloxy$C_{1-6}$alkyl, or phenyl$C_{1-4}$alkyl; or $R^3$ and $R^4$ are taken together with the nitrogen to which they are attached to form a radical of formula (b-1)

with $X_1$ representing $CH_2$ or CHOH; even more in particular $R^3$ and $R^4$ each independently represent hydrogen; $C_{1-6}$alkyl, in particular methyl or ethyl; $C_{1-4}$alkyloxy$C_{1-6}$alkyl, in particular methyloxyethyl; or $R^3$ and $R^4$ are taken together with the nitrogen to which they are attached to form a radical of formula (b-1)

with $X_1$ representing $CH_2$ or CHOH.

An interesting embodiment of the present invention are those compounds of formula (I) or, whenever possible, any subgroup thereof as mentioned hereinbefore or hereinafter as interesting embodiment, wherein $R^3$ and $R^4$ each independently represent hydrogen, $C_{1-6}$alkyl, $C_{1-4}$alkyloxy$C_{1-6}$alkyl, or phenylC$_{1-4}$alkyl; in particular R$^3$ and R$^4$ each independently represent hydrogen, C$_{1-6}$alkyl or C$_{1-4}$alkyloxyC$_{1-6}$alkyl; more in particular R$^3$ and R$^4$ each independently represent hydrogen, methyl, ethyl or methoxyethyl.

An interesting embodiment of the present invention are those compounds of formula (I) or, whenever possible, any subgroup thereof as mentioned hereinbefore or hereinafter as interesting embodiment, wherein R$^3$ and R$^4$ are taken together with the nitrogen to which they are attached to form a radical of formula (b-1) or (b-2)

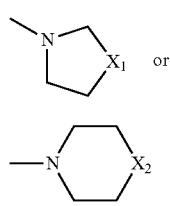

with X$_1$ representing CH$_2$ or CHOH; and X$_2$ representing CH$_2$, O or NR$^6$; in particular wherein R$^3$ and R$^4$ are taken together with the nitrogen to which they are attached to form a radical of formula (b-1) or (b-2)

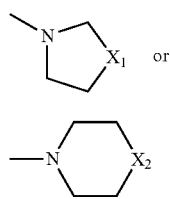

with X$_1$ representing CH$_2$ or CHOH; and X$_2$ representing CH$_2$, O or NH; more in particular wherein R$^3$ and R$^4$ are taken together with the nitrogen to which they are attached to form a radical of formula (b-1) or (b-2)

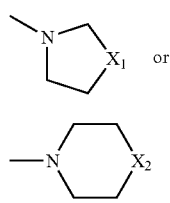

with X$_1$ representing CH$_2$ or CHOH; and X$_2$ representing CH$_2$; even more in particular R$^3$ and R$^4$ are taken together with the nitrogen to which they are attached to form a radical of formula (b-1)

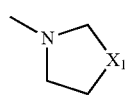

with X$_1$ representing CH$_2$ or CHOH.

An interesting embodiment of the present invention are those compounds of formula (I) or, whenever possible, any subgroup thereof as mentioned hereinbefore or hereinafter as interesting embodiment, wherein R$^5$ represents hydrogen, C$_{1-4}$alkyl, C$_{1-4}$alkyloxy or trifluoromethyl.

An interesting embodiment of the present invention are those compounds of formula (I) or, whenever possible, any subgroup thereof as mentioned hereinbefore or hereinafter as interesting embodiment, wherein R$^5$ represents hydrogen.

An interesting embodiment of the present invention are those compounds of formula (I) or, whenever possible, any subgroup thereof as mentioned hereinbefore or hereinafter as interesting embodiment, wherein R$^5$ represents halo, C$_{1-4}$alkyl, C$_{1-4}$alkyloxy or trifluoromethyl; in particular halo, C$_{1-4}$alkyl or C$_{1-4}$alkyloxy; more in particular halo, methyl or methoxy; even more in particular methyl or methoxy.

An interesting embodiment of the present invention are those compounds of formula (I) or, whenever possible, any subgroup thereof as mentioned hereinbefore or hereinafter as interesting embodiment, wherein n represents an integer of value 0. This means that substituent A is unsubstituted.

An interesting embodiment of the present invention are those compounds of formula (I) or, whenever possible, any subgroup thereof as mentioned hereinbefore or hereinafter as interesting embodiment, wherein n represents an integer of value 1 or 2. This means that substituent A carries 1 or 2 R$^1$ substituents.

An interesting embodiment of the present invention are those compounds of formula (I) wherein A represents phenyl, 1,3-benzodioxolyl, 2,3-dihydro-1,4-benzodioxinyl, pyridyl, pyrimidinyl, quinolinyl; each of said rings optionally being substituted with 1 or 2 substituents each independently selected from halo, hydroxyl, C$_{1-4}$alkyl or C$_{1-4}$alkyloxy; R$^3$ and R$^4$ each independently represent hydrogen, C$_{1-4}$alkyl, C$_{1-4}$alkyl-oxyC$_{1-4}$alkyl, phenylC$_{1-4}$alkyl; or R$^3$ and R$^4$ are taken together with the nitrogen to which they are attached to form pyrrolidinyl optionally substituted in position 3 with hydroxyl; piperidinyl; morpholinyl; piperazinyl optionally substituted with C$_{1-4}$alkyl or C$_{1-4}$alkylcarbonyl; R$^2$ represents hydrogen or methyl; R$^5$ represents hydrogen, halo or C$_{1-4}$alkyloxy, in particular hydrogen, halo or methoxy, even more in particular hydrogen or methoxy.

An interesting embodiment of the present invention are those compounds of formula (I) or, whenever possible, any subgroup thereof as mentioned hereinbefore or hereinafter as interesting embodiment, wherein the substituents on the cycloheptane or oxepine ring have a cis configuration.

An interesting embodiment of the present invention are those compounds of formula (I) wherein the compound is selected from (±) cis-6-(4-Chloro-3-methoxy-phenyl)-5-(3-diethylamino-propyl)-6,7,8,9-tetrahydro-5H-benzocyclohepten-5-ol oxalate;

(±) cis-6-(3-Chloro-phenyl)-5-(3-diethylamino-propyl)-6,7,8,9-tetrahydro-5H-benzocyclohepten-5-ol oxalate;

(±) cis-4-(4-Chloro-3-methoxy-phenyl)-5-(3-diethylamino-propyl)-2,3,4,5-tetrahydro-benzo[b]oxepin-5-ol oxalate;

(±) cis-6-(3-Chloro-phenyl)-5-(3-dimethylamino-propyl)-6,7,8,9-tetrahydro-5H-benzocyclohepten-5-ol oxalate;

(±) cis-6-(4-Chloro-3-methoxy-phenyl)-5-(3-dimethylamino-propyl)-6,7,8,9-tetrahydro-5H-benzocyclohepten-5-ol;

(±) cis-6-(4-Chloro-phenyl)-5-(3-dimethylamino-propyl)-6,7,8,9-tetrahydro-5H-benzocyclohepten-5-ol oxalate;

(±) cis-5-(3-Dimethylamino-propyl)-6-(3-methoxy-phenyl)-6,7,8,9-tetrahydro-5H-benzocyclohepten-5-ol oxalate;

(±) cis-5-(3-Dimethylamino-propyl)-6-(4-fluoro-phenyl)-6,7,8,9-tetrahydro-5H-benzocyclohepten-5-ol oxalate;

(±) cis-5-(3-Dimethylamino-propyl)-6-phenyl-6,7,8,9-tetrahydro-5H-benzocyclohepten-5-ol oxalate;
(±) cis-6-(4-Chloro-3-methoxy-phenyl)-5-{3-[(2-methoxyethyl)-methyl-amino]-propyl}-6,7,8,9-tetrahydro-5H-benzocyclohepten-5-ol oxalate;
(±) cis-5-(3-Dimethylamino-propyl)-6-p-tolyl-6,7,8,9-tetrahydro-5H-benzocyclohepten-5-ol oxalate;
(±) cis-5-(3-Diethylamino-propyl)-6-(4-fluoro-phenyl)-6,7,8,9-tetrahydro-5H-benzocyclohepten-5-ol oxalate;
(±) cis-6-(2,4-Difluoro-phenyl)-5-(3-dimethylamino-propyl)-6,7,8,9-tetrahydro-5H-benzocyclohepten-5-ol oxalate;
(±) cis-4-(4-Chloro-3-methoxy-phenyl)-5-(3-dimethylamino-propyl)-2,3,4,5-tetrahydro-benzo[b]oxepin-5-ol oxalate;
(±) cis-5-(3-Diethylamino-propyl)-6-p-tolyl-6,7,8,9-tetrahydro-5H-benzocyclohepten-5-ol oxalate;
(±) cis-5-(3-Diethylamino-propyl)-6-(3-methoxy-phenyl)-6,7,8,9-tetrahydro-5H-benzocyclohepten-5-ol hydrochloride;
(±) cis-6-(4-Bromo-phenyl)-5-(3-dimethylamino-propyl)-6,7,8,9-tetrahydro-5H-benzocyclohepten-5-ol oxalate;
(±) cis-6-(5-Chloro-pyridin-3-yl)-5-(3-dimethylamino-propyl)-6,7,8,9-tetrahydro-5H-benzocyclohepten-5-ol hydrochloride;
(±) cis-5-(3-Dimethylamino-propyl)-6-quinolin-3-yl-6,7,8,9-tetrahydro-5H-benzocyclohepten-5-ol;
(±) cis-5-(3-Dimethylamino-propyl)-6-(6-methyl-pyridin-3-yl)-6,7,8,9-tetrahydro-5H-benzocyclohepten-5-ol hydrochloride.

An interesting embodiment of the present invention is (±) cis-6-(4-Chloro-phenyl)-5-(3-dimethylamino-propyl)-6,7,8,9-tetrahydro-5H-benzocyclohepten-5-ol oxalate.

The present invention also relates to a compound of formula (II),

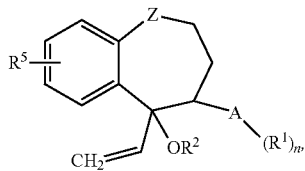

(II)

including any stereochemically isomeric form thereof,
wherein A, Z, $R^1$, $R^2$, $R^5$ and n are defined as for the compounds of formula (I); a N-oxide thereof, a pharmaceutically acceptable salt thereof or a solvate thereof.

In particular, the present invention also relates to a compound of formula (II) wherein the substituents on the cycloheptane or oxepine ring have a cis configuration.

Whenever possible, any interesting embodiment for the compounds of formula (I) as listed hereinabove, also holds for the compounds of formula (II).

In general, compounds of formula (I) can be prepared by reacting an intermediate of formula (II) with an intermediate of formula (III) in the presence of a suitable catalyst, such as for example $Rh(cod)_2BF_4$, optionally in the presence of a second catalyst (for the reduction), such as for example $Ir(cod)_2BF_4$, in the presence of a suitable ligand, such as for example Xantphos or X-Phos, in a suitable solvent, such as for example tetrahydrofuran and an alcohol, e.g. methanol, in the presence of CO and $H_2$ (under pressure) at elevated temperature.

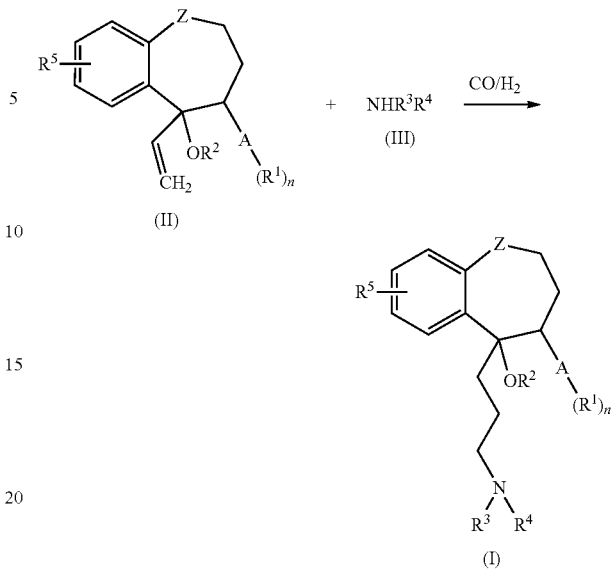

The above reaction can also be performed to form a compound of formula (I-a) from an intermediate of formula (II-a) wherein P represents a suitable protective group, such as for example $—Si(CH_3)_2C(CH_3)_3$, trimethylsilyl, triethylsilyl, benzyl, tetrahydropyranyl. After the reaction, the protective group can be removed, e.g. by treatment with tetrabutylammonium fluoride in case of Si-containing protective groups, to afford the compound of formula (I-a).

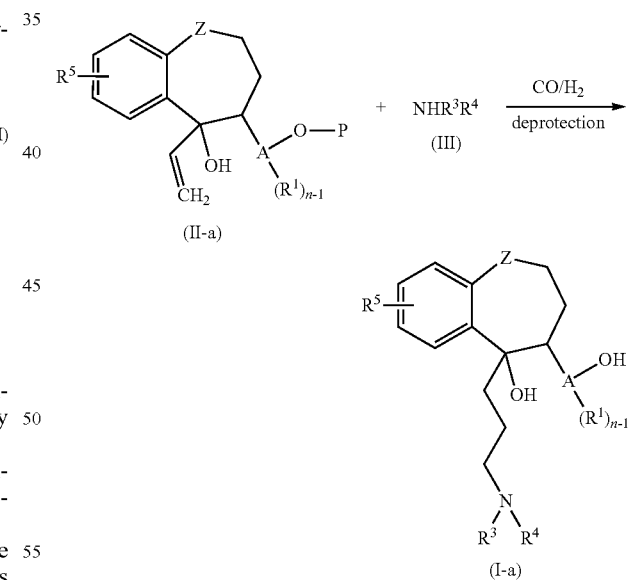

Compounds of formula (I) wherein $R^2$ represents hydrogen, said compounds being represented by formula (I-b), can also be prepared by reacting an intermediate of formula (IV) with an intermediate of formula (V) wherein $W_1$ represents a suitable leaving group, such as for example halo, e.g. chloro, bromo and the like, in the presence of Mg, a suitable initiator of the Grignard reaction such as for example 1,2-dibromoethane or $I_2$ crystals, and a suitable solvent, such as for example tetrahydrofuran or diethylether.

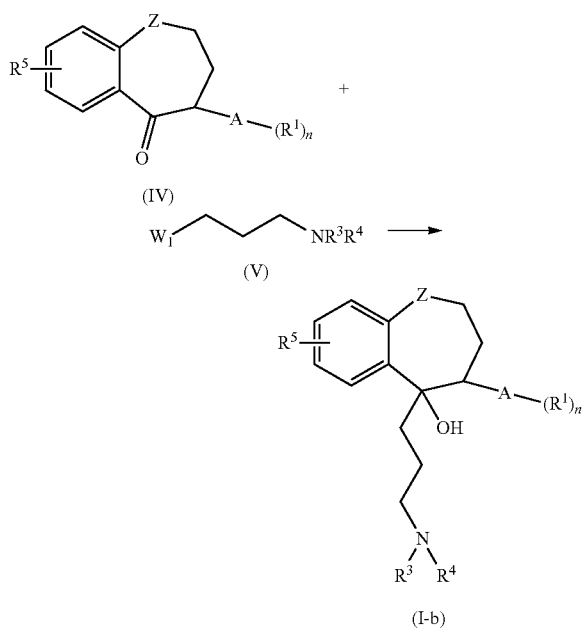

Compounds of formula (I) wherein R³ represents benzyl, said compounds being represented by formula (I-c), can be converted into a compound of formula (I) wherein R³ represents hydrogen, said compounds being represented by formula (I-d), by hydrogenation in the presence of a suitable catalyst, such as for example palladium on charcoal, in the presence of a suitable solvent, such as for example an alcohol, e.g. methanol.

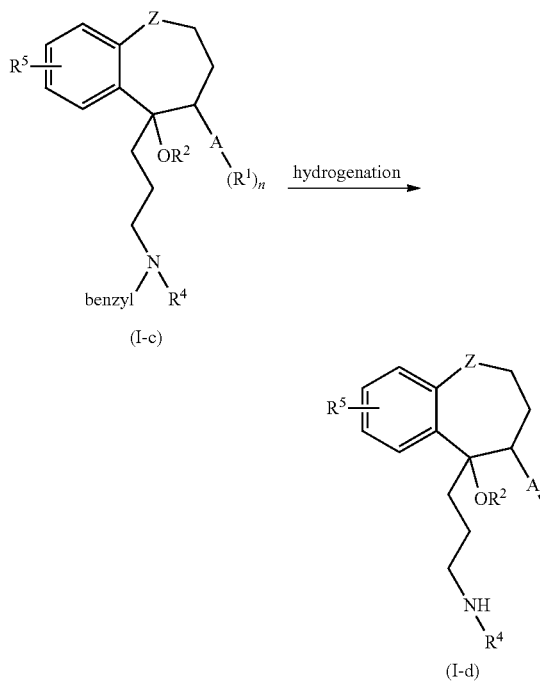

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarbo-peroxoic acid, peroxoalkanoic acids, e.g. peroxoacetic acid, alkylhydroperoxides, e.g. tert-.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The compounds of formula (I) and some of the intermediates in the present invention contain at least two asymmetric carbon atoms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, chiral liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography or SFC (Super Critical Fluid) chromatography, in particular using a chiral stationary phase. The compounds of formula (I) can also be converted into a pharmaceutically acceptable acid addition salt by reaction with an appropriate acid, such as for example hydrochloric acid or oxalic acid, in a suitable solvent, such as for example an alcohol, e.g. 2-propanol, diethylether, diisopropyl ether.

Some of the intermediates and starting materials are known compounds and may be commercially available or may be prepared according to art-known procedures.

In general, intermediates of formula (II) wherein R² represents hydrogen, said intermediates being represented by formula (II-b), can be prepared by reacting an intermediate of formula (IV) with vinylmagnesiumbromide, in the presence of a suitable additive to prevent enolisation, such as for example CeCl₃ or other lanthanide halides, such as other lanthanide chlorides, and a suitable solvent, such as for example tetrahydrofuran. This reaction is preferably performed at reduced temperature, e.g. −78° C. followed by warming up to e.g. room temperature.

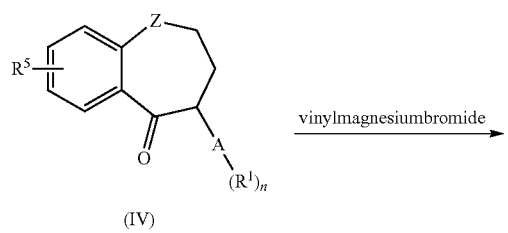

(IV) → vinylmagnesiumbromide

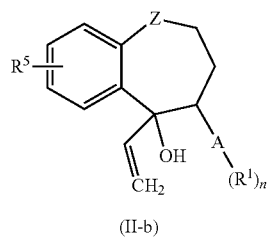

(II-b)

Intermediates of formula (II-b) can be converted into an intermediate of formula (II) wherein $R^2$ represents $C_{1-4}$alkyl, said intermediates being represented by formula (II-c), by reaction with $C_{1-4}$alkyliodide, in the presence of a suitable base, such as for example sodium hydride, and a suitable solvent, such as for example tetrahydrofuran.

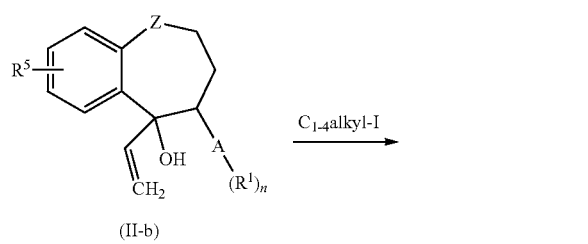

(II-b) → $C_{1-4}$alkyl-I → (II-c)

Intermediates of formula (II-a) can be prepared by reacting an intermediate of formula (IV-a) with vinylmagnesiumbromide, in the presence of a suitable additive to prevent enolisation, such as for example $CeCl_3$ or other lanthanide halides, such as other lanthanide chlorides, and a suitable solvent, such as for example tetrahydrofuran.

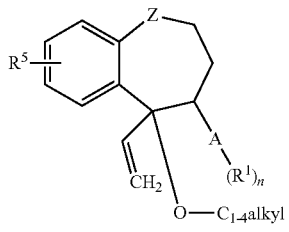

(IV-a) → vinylmagnesiumbromide

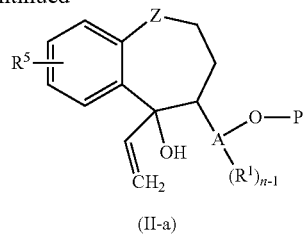

(II-a)

Intermediates of formula (IV) can be prepared by reacting an intermediate of formula (VI) with an intermediate of formula (VII) wherein $W_2$ represents a suitable leaving group, such as for example halo, e.g. bromo and the like, in the presence of a suitable catalyst, such as for example $Pd(OAc)_2$, a suitable ligand, such as for example xantphos or tris-(1,1-dimethylethyl)phosphine, a suitable base, such as for example $Cs_2CO_3$ or sodium tertiary butoxide, and a suitable solvent, such as for example xylene or tetrahydrofuran. The reaction is preferably performed under nitrogen atmosphere and at elevated temperature.

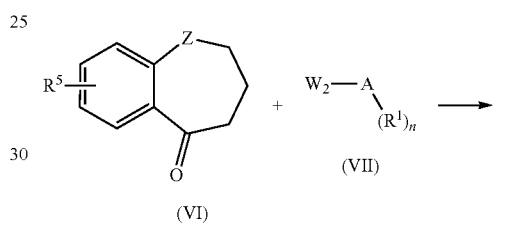

(VI) + (VII) →

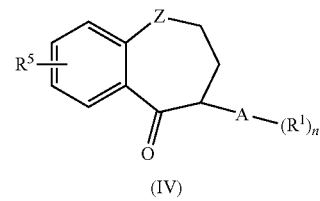

(IV)

Intermediates of formula (IV-a) can be prepared according to the above reaction by reacting an intermediate of formula (VI) with an intermediate of formula (VII-a).

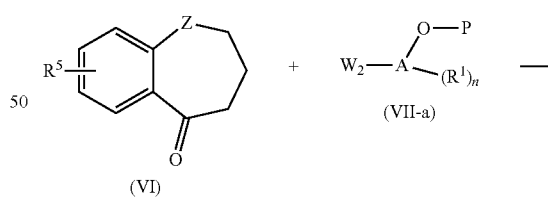

(VI) + (VII-a) →

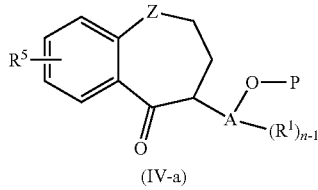

(IV-a)

Intermediates of formula (IV) can also be prepared by reacting an intermediate of formula (VIII) with an intermediate of formula (VII) in the presence of a suitable catalyst, such as for example $Pd(OAc)_2$ in the presence of tri-o-tolylphosphine or dichlorobis(tri-o-tolylphosphine)palladium, tributylmethoxystannane, and a suitable solvent, such as for example toluene, optionally in the presence of KF.

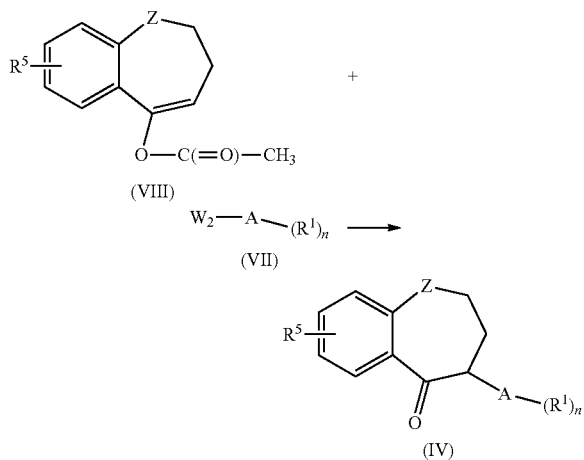

Intermediates of formula (VIII) can be prepared by reacting an intermediate of formula (VI) with $CH_3-C(=O)-O-C(CH_3)=CH_2$ in the presence of a suitable acid, such as for example p-toluenesulfonic acid.

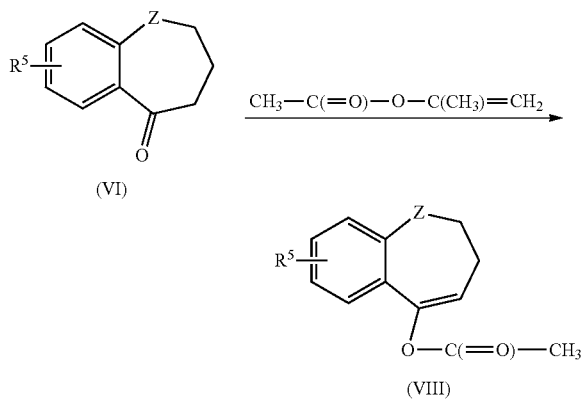

Pharmacological Part

The compounds of formula (I) and any subgroup thereof show ghrelin receptor agonist properties.

Ghrelin is an endogenous peptide hormone discovered in the late 1990s. It is predominantly produced in the stomach and was shown to be the natural ligand for the type 1 growth hormone secretagogue receptor (GHS1A-r) (Kojima et al, Nature 1999, 402:656-660). This G protein-coupled receptor was first cloned only a few years earlier (Howard et al, Science 1996, 273:974-977) and is expressed predominantly in the brain (arcuate and ventromedial nucleus in the hypothalamus, hippocampus and substantia nigra) and in the pituitary. Apart from these tissues, the receptor has also been detected in other areas of the central nervous system and in various peripheral tissues, for instance adrenal and thyroid glands, heart, lung, kidney, skeletal muscles and the gastrointestinal tract.

In the pituitary, activation of GHS1A-r induces secretion of growth hormone, which is believed to be one of the primary functions of the ghrelin-GHS1A-r system. (The GHS1A-r is functionally and structurally different from the growth hormone-releasing hormone (GHRH) receptor.) Another important role of ghrelin mediated signaling has been shown to be stimulation of appetite and feeding behaviour in favour of a positive regulation of energy homeostasis, thereby favouring adiposity, and thus contributing to obesity. As recently suggested, ghrelin may therefore be called the "saginary" (fattening) peptide.

Apart from stimulating growth hormone secretion and positive regulation of energy homeostasis, ghrelin and many synthetic growth hormone secretagogues have also been shown to: 1) exhibit hypothalamic activities that result in stimulation of prolactin (PRL) and ACTH secretion; 2) negatively influence the pituitary-gonadal axis at both the central and peripheral level; 3) influence sleep and behaviour; 4) control gastric motility and acid secretion; 5) modulate pancreatic exocrine and endocrine function and affect glucose levels, 6) modulate cartilage and bone homeostasis, 7) modulate the immune system, as well as 8) have effects on cell proliferation (Van der Lely et al, Endocrine Reviews 2004, 25:426-457; Lago et al, Vitamins and Hormones. 2005, 71:405-432).

The elucidation of these various effects of ghrelin paves the way to therapeutic approaches for the treatment of various diseases in which ghrelin and/or its receptor play a role. Prior to the discovery of ghrelin, efforts in the development of growth hormone secretagogue compounds to treat conditions related to growth hormone deficiencies, have already been going on since the late 1970's (Bowers, Curr. Opin. Endocrinol. Diabetes 2000, 7:168-174). Compounds designed to be orally active for the stimulation of growth hormone release that have been tested in man include small peptides, such as hexarelin (Zentaris) and ipamorelin (Novo Nordisk), and adenosine analogues, as well as small molecules such as capromorelin (Pfizer), L-252,564 (Merck), MK-0677 (Merck), NN7203 (Novo Nordisk), G-7203 (Genentech), S-37435 (Kaken), SM-130868 (Sumitomo) and others. After the identification of ghrelin as the endogenous ligand to GHS1A-r, these compounds have been confirmed to interact with GHS1A-r and to behave as agonists. Many of these compounds were shown in experimental models to exhibit functional effects very similar to those described for ghrelin.

Since the discovery of ghrelin and the subsequent description of the myriad of its various physiological roles and effects, drug discovery efforts have expanded into a broader range of potential therapeutic applications such as digestive disorders requiring pro-kinetic therapy. Examples of such conditions may include idiopathic or diabetic gastroparesis, postoperative ileus, opioid-induced bowel dysfunction, short bowel syndrome, chronic intestinal pseudo-obstruction, emesis, constipation such as associated with the hypomotility phase of irritable bowel syndrome (IBS), delayed gastric emptying associated with wasting conditions, gastro-esophageal reflux disease (GERD), gastric ulcers and other (Murray et al, Gastroenterology 2003, 125:1492-1502). In addition, similar conditions are often encountered in veterinary medicine, implicating that therapeutic agents may also be of use in this area. To name just one example, colic is a gastrointestinal motility dysfunction that constitutes the primary cause of death among horses.

In accordance with literature data, an in house study demonstrated that intravenous administration of ghrelin to mice stimulates gastric emptying of a test meal ($ED_{50}$=0.100 mg/kg, 95% confidence interval 0.058-0.174). But interestingly, ghrelin administered up to 2.5 mg/kg had no effect in transgenic mice with a deletion of GHS1A-r. These observations confirm that the gastrointestinal pro-kinetic properties of ghrelin-ligands are mediated by direct interaction with GHS1A-r. Small molecules showing affinity for the GHS1A-r and activating it are therefore anticipated to stimulate gastrointestinal motility in general, and gastric emptying in particular.

Ghrelin's pro-kinetic activity appears to be independent of the growth hormone-secretory effects and is likely mediated by the vagal-cholinergic muscarinic pathway. The dose levels required are equivalent to those necessary for the hormone's growth hormone secreting and appetite stimulating effects (Peeters, Physiol. Pharmacol. 2003, 54(Suppl. 4):95-103). Apart from effects of GHS1A-r stimulation on the gastrointestinal system, GHS1A-r agonists are also anticipated to affect other systems where ghrelin has been implicated to play an important role in their functioning. These include for instance aspects of reproduction such as control of male and female fertility (anticonception) (ghrelin inhibits secretion of luteinising hormone as well as of testosterone) (Arvat et al, Endocrine 2001, 14:35-43; Barreiro and Tena-Sempre, Mol Cell Endocrinol 2004, 226:1-9); neonatal development where ghrelin influences lactation (Nakahara et al, Biochem Biophys Res Comm 2003, 303:751-755) as well as growth hormone control of postnatal growth in children born small for gestational age (Cianfarani et al, Hormone Research 2006, 65(Suppl 3):70-74); the cardiovascular system (ghrelin is a powerful vasodilator, thus ghrelin agonists have potential for the treatment of chronic heart failure and cardioprotection: Nagaya and Kangawa, Regul. Pept. 2003, 114:71-77, and Curr. Opin. Pharmacol. 2003, 3:146-151; Intl. Pat. Appl. Publ. WO 2004/014412), as well as central nervous system disorders such as anxiety, cognitive impairment (Carlini et al, Biochem. Biophys. Res. Commun 2002, 299:739-743), depression including depressive-like symptoms of chronic stress (Lutter et al., Nature Neuroscience (2008), vol. 11, No. 7: 752-753), neurodegenerative disorders e.g. disorders with neurodegeneration of substantia nigra pars compacta, such as e.g. Parkinson's disease (grhelin was found to have a neuroprotective effect) (Jiang et al., Experimental neurology (2008) 212: 532-537; Dong et al., J. Mol. Neurosci. (2009), 37:182-189; WO2008/143835). Ghrelin's appetite stimulating properties indicate that GHS1A-r agonists may also be useful agents in the treatment of conditions such as cachexia and anorexia nervosa. In addition, based on various other responses to administration of ghrelin that have been described, therapeutic use of ghrelin agonists is also envisaged in disorders such as: patients with low cortisol levels or symptoms of adrencortical insufficiency (stimulation of ACTH-release), disturbances of sleep-wake rhythms (ghrelin promotes wakefulness (Szentirmai et al, Am J Physiol 2007, 292:R575-R585)), exocrine pancreatic insufficiency such as in humans affected with cystic fibrosis or chronic pancreatitis (ghrelin stimulates pancreatic secretion (Am J of Physiol 2006:290:G1350-G1358)), protection of the organ during pancreatitis (Dembinski et al, J Physiol Pharmacol 2003, 54:561-573), osteoporosis (ghrelin directly regulates bone formation) (Fukushima et al, J Bone Min Res 2005:20:790-798)), memory and learning (Diano et al, Nature Neuroscience 2006, 9:381-388).

Based on the above-mentioned observations, the use of ghrelin agonists is believed to be of therapeutic interest, particularly for the treatment of digestive disorders requiring pro-kinetic therapy, such as for example idiopathic or diabetic gastroparesis, postoperative ileus, opioid-induced bowel dysfunction, short bowel syndrome, chronic intestinal pseudo-obstruction, emesis, constipation such as associated with the hypomotility phase of irritable bowel syndrome (IBS), delayed gastric emptying associated with wasting conditions, gastro-esophageal reflux disease (GERD), gastric ulcers, colic; for the treatment of cardiovascular disorders such as for example chronic heart failure or provide cardioprotection, as well as for the treatment of central nervous system disorders such as for example anxiety, cognitive impairment, depression including depressive-like symptoms of chronic stress, neurodegenerative disorders e.g. disorders with neurodegeneration of substantia nigra pars compacta, such as e.g. Parkinson's disease; for stimulating appetite such as in the treatment of cachexia and anorexia nervosa; for the treatment of patients with low cortisol levels or symptoms of adrencortical insufficiency; for the treatment of disturbances of sleep-wake rhythm; for the treatment of exocrine pancreatic insufficiency such as in humans affected with cystic fibrosis or chronic pancreatitis; for the protection of the organ during pancreatitis; for the treatment of osteoporosis; for improving memory and learning. Ghrelin agonists can also be used as anticonceptives.

Due to their GHS1A-r agonistic activity, the compounds of formula (I), their N-oxides, pharmaceutically acceptable salts, or solvates are useful as a medicine, in particular for the treatment or prevention, in particular for the treatment, of a disease, the treatment or prevention of which is affected, mediated or facilitated by activating the GHS1A-r receptor.

In view of the above-described pharmacological properties, the compounds of formula (I), their N-oxides, pharmaceutically acceptable salts or solvates, may be used as a medicine, in particular may be used as a medicine for the treatment or the prevention, in particular for the treatment, of a disease, the treatment or prevention of which is affected, mediated or facilitated by activating the GHS1A-r receptor; more in particular the compounds of formula (I), their N-oxides, pharmaceutically acceptable salts or solvates may be used for the treatment or the prevention, in particular for the treatment, of a disease, the treatment or prevention of which is affected, mediated or facilitated by activating the GHS1A-r receptor. In particular, the present compounds can be used for the manufacture of a medicament for treating or preventing a disease, the treatment or prevention of which is affected, mediated or facilitated by activating the GHS1A-r receptor, in particular for treating a disease, the treatment of which is affected, mediated or facilitated by activating the GHS1A-r receptor. More in particular, the compounds of the invention can be used for the manufacture of a medicament for treating or preventing, in particular treating, a digestive disorder requiring pro-kinetic therapy, such as for example idiopathic or diabetic gastroparesis, postoperative ileus, opioid-induced bowel dysfunction, short bowel syndrome, chronic intestinal pseudo-obstruction, emesis, constipation such as associated with the hypomotility phase of irritable bowel syndrome (IBS), delayed gastric emptying associated with wasting conditions, gastro-esophageal reflux disease (GERD), gastric ulcers, colic; a cardiovascular disorder such as for example chronic heart failure or provide cardioprotection; a central nervous system disorder such as for example anxiety, cognitive impairment, depression including depressive-like symptoms of chronic stress, neurodegenerative disorders e.g. disorders with neurodegeneration of substantia nigra pars compacta, such as e.g. Parkinson's disease; osteoporosis; disturbance of sleep-wake rhythm; exocrine pancreatic insufficiency such as in humans affected with cystic fibrosis or chronic pancreatitis; for stimulating appetite such as in the treatment of cachexia and anorexia nervosa; for the treatment of a patient with low cortisol levels or symptoms of adrencortical insufficiency; for the protection of the organ during pancreatitis; for increasing memory and learning.

In view of the utility of the compounds of formula (I), there is provided a method of treating a warm-blooded mammal, including a human, suffering from or a method of preventing a warm-blooded mammal, including a human, to suffer from a disease, the treatment or prevention of which is affected, mediated or facilitated by activating the GHS1A-r receptor; in particular a method of treating a warm-blooded mammal, including a human, suffering from a disease, the treatment of which is affected, mediated or facilitated by activating the GHS1A-r receptor. Said methods comprise the administration of an effective amount of a compound of formula (I), a N-oxide form thereof, a pharmaceutically acceptable salt thereof or a solvate thereof, to a warm-blooded mammal, including a human.

The present invention also provides compositions for preventing or treating a disease, the treatment or prevention of which is affected, mediated or facilitated by activating the GHS1A-r receptor; in particular for treating a disease, the treatment of which is affected, mediated or facilitated by activating the GHS1A-r receptor. Said compositions comprise a therapeutically effective amount of a compound of formula (I), a N-oxide form thereof, a pharmaceutically acceptable salt thereof or a solvate thereof, and a pharmaceutically acceptable carrier or diluent.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the active ingredient, and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXPERIMENTAL PART

Hereinafter, the term "DCM" means dichloromethane, "MeOH" means methanol, "EtOAc" means ethyl acetate, "DIPE" means diisopropyl ether, "THF" means tetrahydrofuran, "LCMS" means Liquid Chromatography/Mass spectrometry, "eq." means equivalent, "HPLC" means high-performance liquid chromatography, "r.t." means room temperature, "Rh(COD)$_2$BF$_4$" means bis[(1,2,5,6-η)-1,5-cyclooctadiene]rhodium(1+) tetrafluoroborate(1−), "Ir(COD)$_2$BF$_4$" means bis[(1,2,5,6-η)-1,5-cyclooctadiene]iridium(1+) tetrafluoroborate(1−), "Pd(OAc)$_2$" means palladium acetate, "X-Phos" means dicyclohexyl[2',4',6'-tris(1-methylethyl)[1,1'-biphenyl]-2-yl]-phosphine, "Xantphos" means (9,9-dimethyl-9H-xanthene-4,5-diyl)bis[diphenyl-phosphine], "SFC" means supercritical fluid chromatography, "MeI"

means methyl iodide, "NH₄OAc" means ammonium acetate, "q.s." means quantum sufficit and "r.t." means room temperature.

A. Preparation of the Intermediates

Example A1 a-1) Preparation of Intermediate 1

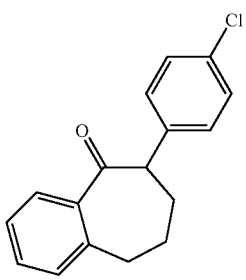 [SMILES: O=C1c2ccccc2CCCC1c1ccc(Cl)cc1]

A mixture of 6,7,8,9-tetrahydro-5H-benzocyclohepten-5-one (37.2 ml, 0.2480 mol), 1-bromo-4-chlorobenzene (47.4 g, 0.2480 mol) and $Cs_2CO_3$ (179.2 g) in xylene (600 ml) was mixed and flushed with $N_2$. $Pd(OAc)_2$ (2.8 g) and X-Phos (11.6 g) were added and the reaction mixture was heated to 150° C. Subsequently the mixture was cooled to r.t. and filtered. The filtrate was diluted with DCM. This organic mixture was washed with an aqueous $NH_4Cl$ solution, dried ($MgSO_4$), filtered and the solvent was evaporated. The residue was purified by distillation (Kugelrohr Distillation) to yield 44 g of intermediate 1 (66%).

a-2) Preparation of Intermediate 1

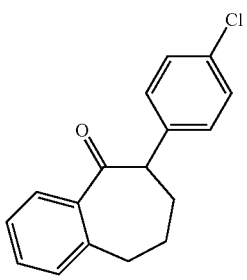 [SMILES: O=C1c2ccccc2CCCC1c1ccc(Cl)cc1]

A mixture of THF (100 ml), $Pd(OAc)_2$ (1.4 g, 0.0062 mol) and sodium tert-butoxide (8.3 g, 0.0870 mol) was stirred for 15 minutes at r.t. under $N_2$ atmosphere. Then first tris(1,1-dimethylethyl)phosphine (1.3 g, 0.0062 mol) was added, subsequently 1-bromo-4-chlorobenzene (10.8 g, 0.0560 mol) was added and finally 6,7,8,9-tetrahydro-5H-benzocyclohepten-5-one (10 g, 0.0624 mol) was added. The reaction mixture was slowly warmed up to 50° C. and the mixture was kept at this temperature for 3 hours after which it was stirred overnight at r.t. The mixture was warmed up again for 4 hour at 75° C. and was then cooled to r.t. The mixture was quenched with a saturated $NH_4Cl$ solution and was extracted 3× with DCM. The combined organic extracts were washed ($H_2O$), dried ($MgSO_4$), filtered and the solvent was evaporated. The residue was purified on silica gel (eluent: DCM). The pure fractions were concentrated in vacuo. The residue was triturated in n-hexane. The precipitate was filtered off and dried (40° C., 2 hours) to yield 2.9 g of intermediate 1.

b) Preparation of Intermediate 2

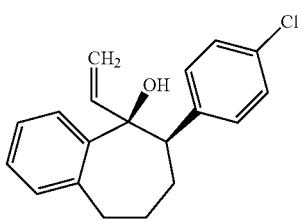 [SMILES: C=C[C@@]1(O)c2ccccc2CCC[C@@H]1c1ccc(Cl)cc1]

CIS, relative stereochemistry $CeCl_3$ (112 g, 0.450 mol) was dried overnight at 140° C. and was then cooled to r.t. and stirred in THF (q.s) for 90 minutes. The white slurry was cooled to −78° C. and vinylmagnesium bromide (0.7 M in THF) (450 ml, 0.315 mol) was added dropwise over 30 minutes. The light orange slurry was stirred for 30 minutes and a mixture of intermediate 1 (40 g, 0.150 mol) in THF (500 ml) was added dropwise over 30 minutes. The reaction mixture was allowed to warm up slowly overnight to r.t. Subsequently, the mixture was quenched with an aqueous $NH_4Cl$ solution. The gummy residue was filtered off and washed with ether. The layers were separated and the aqueous phase was extracted with ether. The combined organic layers were washed ($H_2O$), dried ($MgSO_4$), filtered and the filtrate was evaporated to yield a thick brown oil. Yield: Intermediate 2.

c) Preparation of Intermediate 14

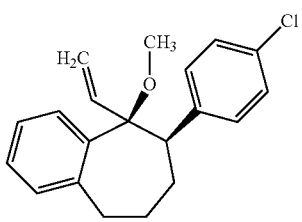 [SMILES: C=C[C@@]1(OC)c2ccccc2CCC[C@@H]1c1ccc(Cl)cc1]

CIS, relative stereochemistry

Intermediate 2 (1 g, 0.0033 mol) was stirred in THF (50 ml). NaH (0.3 g, 0.006 mol) was added and the reaction mixture was stirred for 30 minutes. MeI was added and the reaction mixture was stirred overnight. Subsequently, the mixture was concentrated, washed ($H_2O$), dried, filtered and the solvent was evaporated (in vacuo). The residue was purified by column chromatography over silica gel (eluent: DCM/ heptane 50/50). The product fractions were collected and the solvent was evaporated. Yield: 0.7 g of intermediate 14.

Example A2 a) Preparation of Intermediate 3

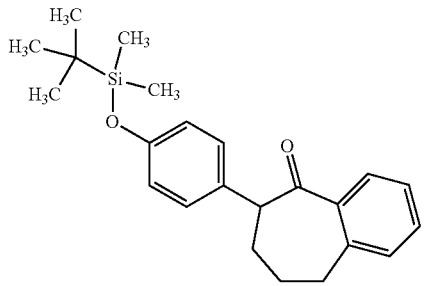 [SMILES: CC(C)(C)[Si](C)(C)Oc1ccc(C2CCCc3ccccc3C2=O)cc1]

A mixture of 6,7,8,9-tetrahydro-5H-benzocyclohepten-5-one (18.6 ml, 0.124 mol), (4-bromophenoxy)-tert-butyldimethylsilane (30.34 ml, 0.124 mol) and CsCO₃ (89.6 g) in xylene (400 ml) was mixed and flushed with $N_2$. Subsequently, Pd(OAc)₂ (1.4 g) and X-Phos (5.80 g) were added and the reaction mixture was heated to 150° C. and was stirred overnight at 80° C. The mixture was cooled to r.t., filtered, diluted with DCM, washed (NH₄Cl solution), dried (MgSO₄), filtered and the solvent was evaporated. After working-up, the residue was purified by reversed-phase HPLC (Shandon Hyperprep® C18 BDS (Base Deactivated Silica) 8 μm, 250 g, I.D. 5 cm). A gradient with 3 mobile phases was applied. Phase A: a 0.25% NH₄HCO₃ solution in water; phase B: MeOH; phase C: CH₃CN). The desired fractions were collected. After working-up, 6.61 g of intermediate 3 was obtained.

b) Preparation of Intermediate 4

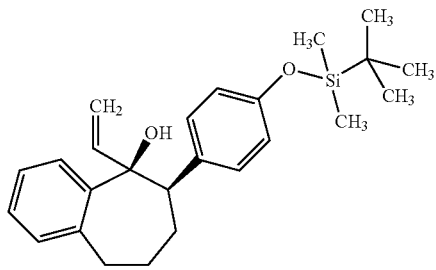 [SMILES: C=C[C@@]1(O)c2ccccc2CCC[C@@H]1c1ccc(O[Si](C)(C)C(C)(C)C)cc1]

CIS, relative stereochemistry

CeCl₃ (14.7 g) was stirred in THF (150 ml; dry) to form a slurry. This mixture was stirred for 2 hours. Then vinylmagnesium bromide (0.7 M in THF) (57 ml, 0.040 mol) was added dropwise over 15 minutes at −78° C. Subsequently, intermediate 3 (6.61 g, 0.018 mol) was added dropwise over 90 minutes and the mixture was stirred at −78° C. for 2 hours. Next, the reaction mixture was warmed up slowly to r.t. (overnight). Then, the mixture was cooled again to 0° C. and quenched with a NH₄Cl solution. The mixture was filtered over Dicalite. The solvent was evaporated and DCM was added to the residue. This organic mixture was washed (NH₄Cl solution), dried (MgSO₄), filtered and the solvent was evaporated. The crude compound was purified by flash column chromatography (eluent: from heptane to DCM). The desired fractions were collected and the solvent was evaporated. Yield: 6.05 g of intermediate 4 (85%).

Example A3 a) Preparation of Intermediate 5

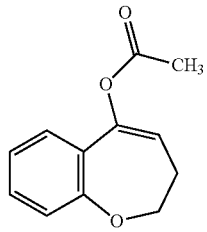

A mixture of 2,3,4,5-tetrahydro-1-benzoxepin-5-one (2 g, 0.0120 mol), 2-acetoxy-1-propene (2.9 ml, 0.0260 mol) and p-toluenesulfonic acid (0.24 g, 0.0010 mol) was stirred and refluxed overnight. EtOAc was added. The organic layer was washed with K₂CO₃ (10% solution), dried (MgSO₄), filtered and the solvent was evaporated. The residue (3.2 g) was purified by column chromatography over silica gel (eluent: cyclohexane/EtOAc 95/5; 15-40 μm). The pure fractions were collected and the solvent was evaporated. Yielding: 2.6 g of intermediate 5 (100%).

b) Preparation of Intermediate 6

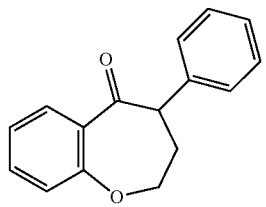 [SMILES: O=C1c2ccccc2OCCC1c1ccccc1]

A solution of Pd(OAc)₂ (0.03 g, 0.0001 mol) and tri-O-tolylphosphine (0.08 g, 0.0002 mol) was added to a solution of intermediate 5 (2.6 g, 0.0130 mol) in toluene (25 ml). Subsequently bromobenzene (1.5 ml, 0.0140 mol) and tributylmethoxystannane (3.7 ml, 0.0130 mol) were added and the reaction mixture was stirred and refluxed overnight. K₂CO₃ was added and the mixture was filtered over Celite. The Celite was washed with EtOAc. The filtrate was washed (aqueous saturated NaCl solution), dried (MgSO₄), filtered and the solvent was evaporated. The residue (2.7 g) was purified by column chromatography over silica gel (eluent: cyclohexane/

EtOAc 97/3; 15-40 μm). The pure fractions were collected and the solvent was evaporated. Yield: 1.1 g of intermediate 6. (36%).

Example A4 a) Preparation of Intermediate 7

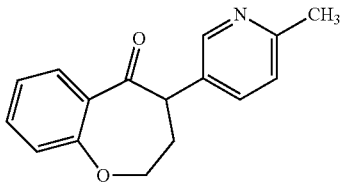

A mixture of 2,3,4,5-tetrahydro-1-benzoxepin-5-one (3.8 g, 0.023 mol), 5-bromo-2-methylpyridine (4 g, 0.023 mol), Cs$_2$CO$_3$ (18 g) and xylene (100 ml) was stirred and flushed with N$_2$ during 20 minutes. Pd(OAc)$_2$ (0.27 g) and X-Phos (1.18 g) were added and the reaction mixture was stirred and refluxed under N$_2$ atmosphere during 5 hours. Then, the mixture was cooled and filtered. The filtrate was washed with an aqueous NH$_4$Cl solution. The organic layer was dried and concentrated. The residue was purified over silica gel (eluent: DCM/MeOH 95/5). The product fractions were collected and the solvent was evaporated. Yield: 4.5 g of intermediate 7.

b) Preparation of Intermediate 8

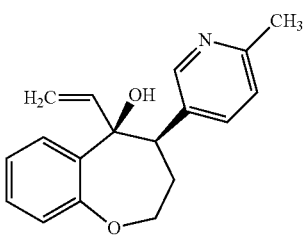 [SMILES: C=C[C@@]1(O)c2ccccc2OCC[C@@H]1c1ccc(C)nc1]

CIS, relative stereochemistry

CeCl$_3$ (5.9 g) was dried overnight in vacuo at 140° C. The dried CeCl$_3$ was stirred in THF (60 ml) for 2 hours under N$_2$ atmosphere. This mixture was cooled to −78° C. and vinylmagnesium bromide (32 ml, 0.032 mol; 1M solution in THF) was added over a period of 10 minutes. Subsequently intermediate 7 (2.2 g, 0.008 mol) in THF (50 ml) was added over 30 minutes. The reaction mixture was allowed to warm up to r.t. and was stiffed for 1 hour. Then, the reaction mixture was cooled on ice and an aqueous NH$_4$Cl solution (6 ml) was added. The reaction mixture was stirred for 1 hour and was then filtered. The filtrate was dried, filtered and the filtrate's solvent was evaporated. The residue was purified over silica gel (eluent: DCM/MeOH 98/2). The product fractions were collected and the solvent was evaporated. Yield: 1.2 g of intermediate 8.

Example A5 a) Preparation of Intermediate 9

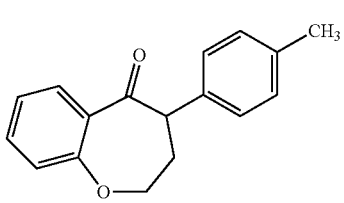 [SMILES: Cc1ccc(C2CCOc3ccccc3C2=O)cc1]

A mixture of 1-bromo-4-methylbenzene (3.2 g, 0.018709 mol), 2,3,4,5-tetrahydro-1-benzoxepin-5-one (3 g, 0.018497 mol), Cs$_2$CO$_3$ (18 g, 0.055245 mol) and xylene (100 ml) was stiffed and flushed with N$_2$ during 20 minutes. Pd(OAc)$_2$ (0.27 g, 0.000456 mol) and X-Phos (1.18 g) were added and the reaction mixture was refluxed under N$_2$ for 5 hours. Then, the mixture was cooled and filtered. The filtrate was washed with a NH$_4$Cl solution. The organic layer was dried and concentrated. The residue was purified over silica gel (eluent: DCM). The desired fractions were collected and the solvent was evaporated. Yield: 4 g of intermediate 9 (85.7%).

b) Preparation of Intermediate 10

CIS, relative stereochemistry

CeCl$_3$ (10.8 g, 0.043818 mol) was dried overnight in vacuo at 140° C. The dried CeCl$_3$ was stirred in THF (150 ml) during 2 hours (under N$_2$ atmosphere). Then the mixture was cooled to −78° C. and vinylmagnesium bromide (4 equivalents; 1 M solution in THF) was added in 10 minutes. Subsequently, intermediate 9 (4 g, 0.015853 mol) and THF (50 ml) in 30 minutes. The reaction mixture was allowed to warm up to r.t. and was stiffed overnight. Then the mixture was cooled on ice and 10 ml of a NH$_4$Cl solution was added. The mixture was stirred for 1 hour and was then filtered. The filtrate was dried, filtered and the solvent was evaporated. The residue was purified by column chromatography over silica gel (eluent:

DCM). The desired fractions were collected and the solvent was evaporated. Yield: 3.4 g of intermediate 10 (76.5%).

Example A6 a) Preparation of Intermediate 11

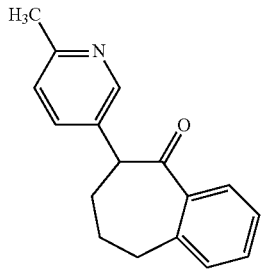 [SMILES: Cc1ccc(C2CCCc3ccccc3C2=O)cn1]

A mixture of 6,7,8,9-tetrahydro-5H-benzocyclohepten-5-one (1.6 g, 0.010 mol), 5-bromo-2-methylpyridine (1.7 g, 0.010 mol), Pd(OAc)$_2$ (0.11 g, 0.0005 mol), X-Phos (0.477 g, 0.001 mol) and Cs$_2$CO$_3$ (6.5 g, 0.022 mol) in xylene (q.s.) was heated overnight at 140° C. Then the reaction mixture was cooled, the solvent was evaporated and the residue was purified by Biotage column chromatography eluting with a gradient 0-5% MeOH/DCM. The product fractions were collected and the solvent was evaporated, yielding intermediate 11.

b) Preparation of Intermediate 12

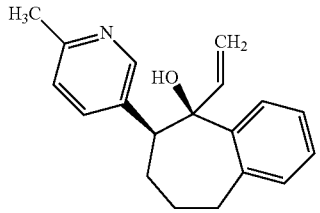 [SMILES: C=C[C@]1(O)c2ccccc2CCC[C@H]1c1ccc(C)nc1]

CIS, relative stereochemistry

CeCl$_3$ (7.46 g, 0.020 mol) was dried at 80° C. under 0.02 mBar for 2 hours, then at 110° C. for 1 hour and finally at 140° C. for 2 hours. After cooling, the white powder was stirred in dry THF (75 ml) under N$_2$ atmosphere at r.t. for 90 minutes. This white suspension was cooled down to −78° C. and vinylmagnesium bromide (0.7 M in THF) (20 ml) was added dropwise to obtain a light yellow suspension. Afer 1 hour, intermediate 11 (1.65 g, 0.00657 mol) in THF (q.s.) was added dropwise at −78° C. and the mixture was stirred for 1 hour. Subsequently, the mixture was warmed up to −20° C. and the mixture was quenched with an aqueous NH$_4$Cl solution. Then the mixture was diluted with additional H$_2$O and was filtered through Celite. The filtrate was extracted with ether, dried (MgSO$_4$), filtered and the filtrate was evaporated. The residue was purified by column chromatography over silica gel eluting with 5% MeOH/DCM. The product fractions were collected and the solvent was evaporated. The resulting oil was taken up in DIPE and n-heptane was added. A solid crystallized that was filtered off and dried. Yield: 1.12 g of intermediate 12 (off-white solid).

Example A7

Preparation of Intermediate 13

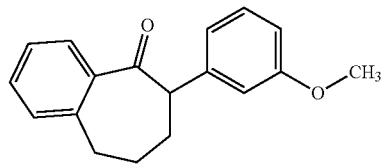 [SMILES: COc1cccc(C2CCCc3ccccc3C2=O)c1]

A mixture of 6,7-dihydro-5H-benzocyclohepten-9-ol acetate (3 g, 0.0150 mol), 1-bromo-3-methoxybenzene (2.2 ml, 0.0180 mol), dichlorobis(tri-o-tolylphosphine)-palladium (0.23 g, 0.0082 mol) and tributylmethoxystannane (0.23 g, 0.0082 mol) in toluene (30 ml) was stirred and refluxed overnight. KF (10%) was added and the mixture was stirred overnight at r.t. The precipitate was filtered over Celite. The Celite was washed with EtOAc. The filtrate was extracted with EtOAc and the combined organic layers were washed (with aqueous saturated NaCl solution). The separated organic layer was dried (MgSO$_4$), filtered and the solvent was evaporated. The residue was purified by column chromatography over silica gel (eluent: cyclohexane/EtOAc 95/5 to 90/10; 20-45 μm). The pure fractions were collected and the solvent was evaporated, yielding 1.8 g of intermediate 13 (45%).

Example A8 a) Preparation of Intermediate 15

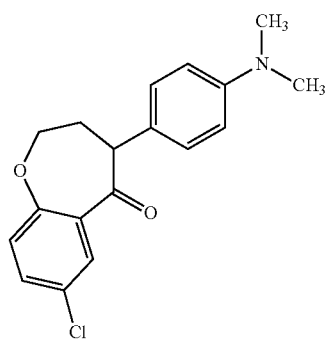 [SMILES: CN(C)c1ccc(C2CCOc3ccc(Cl)cc3C2=O)cc1]

A mixture of 7-chloro-3,4-dihydro-1-benzoxepin-5(2H)-one (9.8 g, 0.050 mol), 4-bromo-N,N-dimethyl-benzeneamine (9.5 g, 0.050 mol), X-Phos (2.4 g), Cs$_2$CO$_3$ (4.11 g) and Pd(OAc)$_2$ (0.65 g) in xylene (150 ml) was heated to 110-120° C. for 6 hours under N$_2$ atmosphere. After reaction, the mixture was filtered and the solvent was evaporated. The residue was purified by column chromatography (eluent: petroleum ether/EtOAc 1/1). The desired fractions were collected and the solvent was evaporated. The residue was crystallized from ethanol to give 8.2 g of intermediate 15 as a purple solid (51.9% yield).

b) Preparation of Intermediate 16

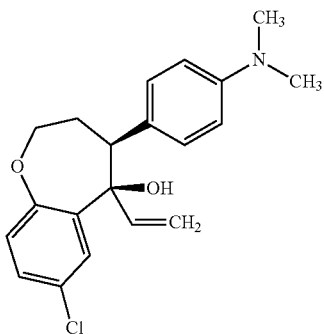 [SMILES: C=C[C@]1(O)c2cc(Cl)ccc2OCC[C@H]1c1ccc(N(C)C)cc1]

CIS, relative stereochemistry

CeCl$_3$ (0.0239 mol) is dried overnight in vacuo at 140° C. The dried CeCl$_3$ is stirred in THF (60 ml) for 2 hours under N$_2$ atmosphere. This mixture is cooled to −78° C. and vinylmagnesium bromide (0.032 mol; 1M solution in THF) is added over a period of 10 minutes. Subsequently intermediate 15 (0.008 mol) in THF (50 ml) is added over 30 minutes. The reaction mixture is allowed to warm up to r.t. and is stirred for 1 hour. Then, the reaction mixture is cooled on ice and an aqueous NH$_4$Cl solution (6 ml) is added. The reaction mixture is stirred for 1 hour and is then filtered. The filtrate is dried, filtered and the filtrate's solvent is evaporated. The residue is purified by column chromatography. Yield: Intermediate 16.

Example A9 a) Preparation of Intermediate 17

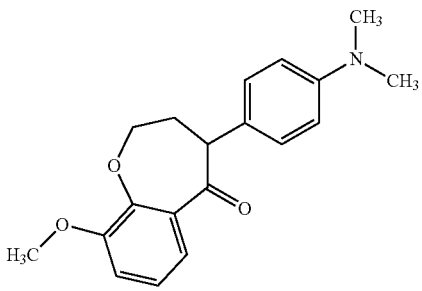

A mixture of 3,4-dihydro-9-methoxy-1-benzoxepin-5 (2H)-one (1.92 g, 0.010 mol), 4-bromo-N,N-dimethyl-benzeneamine (2.0 g, 0.010 mol), X-Phos (0.48 g), Cs$_2$CO$_3$ (6.54 g) and Pd(OAc)$_2$ (0.12 g) in xylene (40 ml) was heated to 110-120° C. for 12 hours under N$_2$ atmosphere. After reaction, the mixture was filtered and the solvent was evaporated. The residue was purified by column chromatography (eluent: petroleum ether/EtOAc 10/1). The desired fractions were collected and the solvent was evaporated. The residue was crystallized from ethanol to give 1.2 g of intermediate 17 as a white solid (38.7% yield).

b) Preparation of Intermediate 18

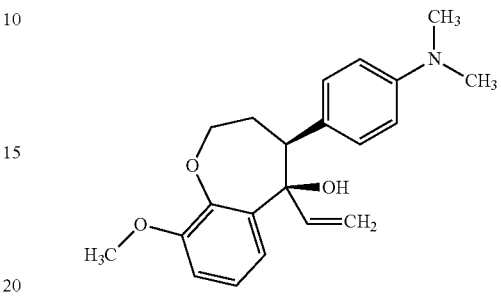

CIS, relative stereochemistry

CeCl$_3$ (0.0239 mol) is dried overnight in vacuo at 140° C. The dried CeCl$_3$ is stirred in THF (60 ml) for 2 hours under N$_2$ atmosphere. This mixture is cooled to −78° C. and vinylmagnesium bromide (0.032 mol; 1M solution in THF) is added over a period of 10 minutes. Subsequently intermediate 17 (0.008 mol) in THF (50 ml) is added over 30 minutes. The reaction mixture is allowed to warm up to r.t. and is stirred for 1 hour. Then, the reaction mixture is cooled on ice and an aqueous NH$_4$Cl solution (6 ml) is added. The reaction mixture is stirred for 1 hour and is then filtered. The filtrate is dried, filtered and the filtrate's solvent is evaporated. The residue is purified by column chromatography. Yield: Intermediate 18.

Tables 1 to 3 list compounds of formula (II), which were prepared by analogy to the above examples (Ex. No.) and were used for the synthesis of the compounds of formula (I).

TABLE 1

(±)-CIS (5S, 6R; 5R, 6S)
(relative stereochemistry)

| Int. No. | Ex. No. | R$^2$ | A—(R$^1$)$_n$ |
|---|---|---|---|
| 19 | A1.b | - - -H | |
| 20 | A1.b | - - -H | CH$_3$ |

TABLE 1-continued

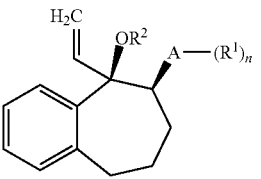

(±)-CIS (5S, 6R; 5R, 6S)
(relative stereochemistry)

| Int. No. | Ex. No. | R² | A—(R¹)ₙ |
|---|---|---|---|
| 21 | A1.b | ---H | 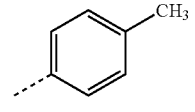 4-CH₃-phenyl |
| 22 | A1.b | ---H | 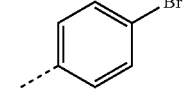 4-Br-phenyl |
| 23 | A1.b | ---H | 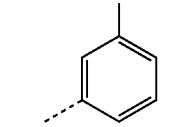 3-Cl-phenyl |
| 2 | A1.b | ---H | 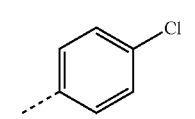 4-Cl-phenyl |
| 14 | A1.c | ---CH₃ | 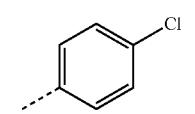 4-Cl-phenyl |
| 24 | A1.b | ---H | 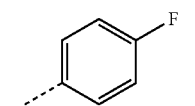 4-F-phenyl |
| 25 | A1.b | ---H | 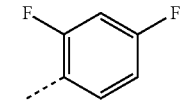 2,4-diF-phenyl |
| 26 | A1.b | ---H | 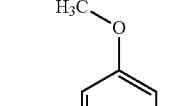 3-OCH₃-phenyl |
| 27 | A1.b | ---H | 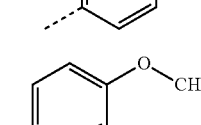 4-OCH₃-phenyl |
| 28 | A1.b | ---H | 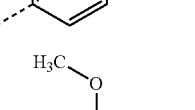 2-Cl-5-OCH₃-phenyl |
| 29 | A1.b | ---H | 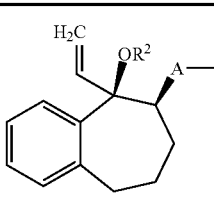 3,4-diOCH₃-phenyl |
| 4 | A2.b | ---H | 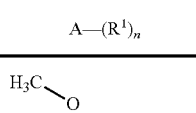 4-(OTBDMS)-phenyl |
| 30 | A1.b | ---H | 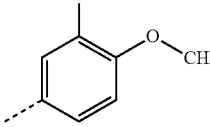 2-methyl-pyridin-5-yl |
| 31 | A1.b | ---H | 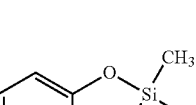 5-chloro-pyridin-3-yl |
| 32 | A1.b | ---H | 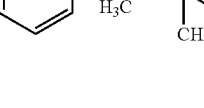 5-methoxy-pyridin-3-yl |
| 33 | A1.b | ---H | 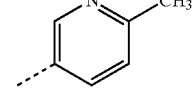 pyrimidin-5-yl |
| 34 | A1.b | ---H | 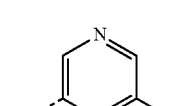 quinolin-3-yl |
| 35 | A1.b | ---H | 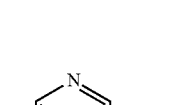 benzo[1,3]dioxol-5-yl |

TABLE 2

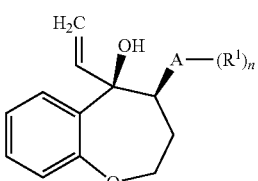

(±)-CIS (4R, 5S; 4S, 5R)
(relative stereochemistry)

| Int. No. | Ex. No. | A—(R¹)ₙ |
|---|---|---|
| 10 | A5.b |  4-CH₃-phenyl |
| 36 | A5.b |  4-Cl-phenyl |
| 37 | A5.b | 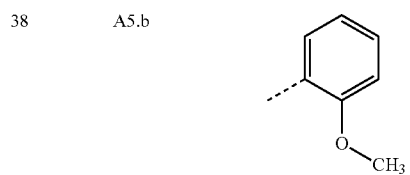 3,4-diF-phenyl |
| 38 | A5.b | 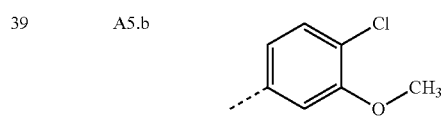 2-OCH₃-phenyl |
| 39 | A5.b |  4-Cl-3-OCH₃-phenyl |
| 8 | A4.b | 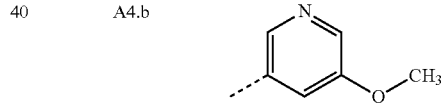 5-Cl-pyridin-3-yl |
| 40 | A4.b | 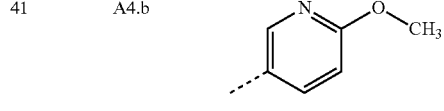 5-OCH₃-pyridin-3-yl |
| 41 | A4.b | 2-OCH₃-pyridin-5-yl |

TABLE 3

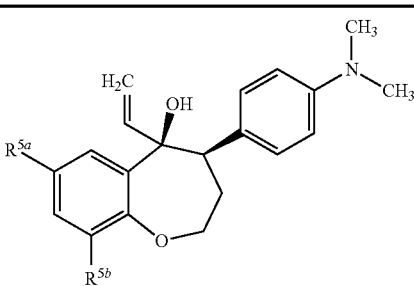

(±)-CIS (4R, 5S; 4S, 5R)
(relative stereochemistry)

| Int. No. | Ex. No. | R^{5a} | R^{5b} |
|---|---|---|---|
| 16 | A8.b | —Cl | - - -H |
| 18 | A9.b | - - -H | - - -OCH₃ |

B. Preparation of the Compounds

Example B1 a-1) Preparation of Compounds 1, 3 and 4

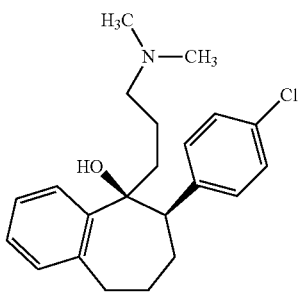 [SMILES: CN(C)CCC[C@@]1(O)c2ccccc2CCC[C@@H]1c1ccc(Cl)cc1]

Compound 1 (CIS, relative stereochemistry; free base)
Compound 3 ($[\alpha]_D^{20}$=+8.02° (0.6112 w/v %, DMF); oxalate salt)
Compound 4 ($[\alpha]_D^{20}$=−7.69° (0.5335 w/v %, DMF); oxalate salt)

A mixture of intermediate 2 (15 g, 0.050 mol), Rh(COD)₂BF₄ (0.02 g), Ir(COD)₂BF₄ (0.05 g) and Xantphos (0.12 g) in dimethylamine (30% in MeOH) (8 ml), THF (50 ml) and MeOH (50 ml) under CO/H₂ (7/33 atm) atmosphere was stirred for 32 hours at 100° C. Subsequently the reaction mixture was concentrated and the residue was purified by column chromatography (eluent: first DCM; then 5% MeOH/DCM; finally 10% (MeOH/NH₃)/DCM). The pure fractions were collected yielding 4 g of a yellow oil which crystallized on standing. The solid was triturated in heptane and collected by filtration. The product was dried overnight (50° C., vacuum), yielding 2.24 g of compound 1 as a cream solid (CIS mixture). A second fraction crystallized from the filtrate yielding a second batch (0.390 g) of compound 1 as white crystals (CIS mixture). A part of the first batch (2 g) of compound 1 was further separated into its enantiomers by preparative SFC (load: 55 mg/1.5 ml; Chiralpak AD-H column (30×250 mm); mobile phase (hold for 9 minutes): 25% MeOH (+0.2% 2-propylamine)/75% CO$_2$); flow: 50 ml/min; column heater temperature: 40° C.; nozzle pressure: 100 bar). Two different product fractions were collected and the solvent was evaporated. The compound that was eluted first from the column (as a free base), was crystallized as an oxalate salt yielding 1.00 g of compound 3. The compound that was eluted second from the column (as a free base), was crystallized as an oxalate salt yielding 1.00 g of compound 4.

a-2) Preparation of Compounds 2, 3 and 4

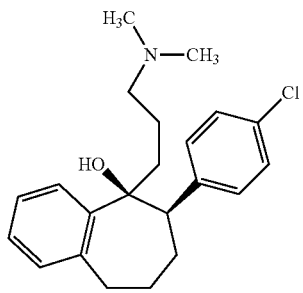 [SMILES: CN(C)CCC[C@@]1(O)c2ccccc2CCC[C@@H]1c1ccc(Cl)cc1]

Compound 2 (CIS, relative stereochemistry; oxalate salt)
Compound 3 ([α]$_D^{20}$=+8.02° (0.6112 w/v %, DMF); oxalate salt)
Compound 4 ([α]$_D^{20}$=−7.69° (0.5335 w/v %, DMF); oxalate salt)

A mixture of intermediate 2 (5 g, 0.016 mol), dimethylamine (30% in MeOH) (3 ml), Rh(COD)$_2$BF$_4$ (0.008 g), Ir(COD)$_2$BF$_4$ (0.02 g) and Xantphos (0.048 g) in MeOH/toluene (40 ml; 1/1) under CO/H$_2$ (7/33 atm) atmosphere was reacted for 32 hours at 100° C. This reaction was performed 4 times. The combined batches were purified by column chromatography on silica gel (eluent: first DCM; then 5% MeOH/DCM; finally 5% (MeOH/NH$_3$)/DCM). The desired fractions were collected and the solvent was evaporated, yielding 15 g of a crude oil. This oil was taken up in 2-propanol and treated with oxalic acid. The solid was collected and dried under vacuum, yielding 10 g of compound 2 a white solid (CIS mixture). Compound 2 was separated into enantiomers by preparative SFC (Chiralpak AD-H column (30×250 mm); mobile phase: 28% MeOH (+0.2% 2-propylamine)/72% CO$_2$); flow: 50 ml/min; column heater temperature: 40° C.; nozzle pressure: 100 bar). Two different product fractions were collected and the solvent was evaporated. The compound that was eluted first from the column, was converted to the oxalate. Yield: 4.1 g of compound 3. The compound that was eluted second from the column, was converted to the oxalate. Yield: 4.05 g of compound 4.

b) Preparation of Compounds 1, 3, 4, 5 and 6

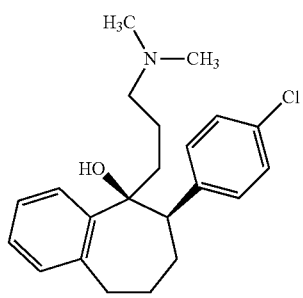 [SMILES: CN(C)CCC[C@@]1(O)c2ccccc2CCC[C@@H]1c1ccc(Cl)cc1]

Compound 1 (CIS, relative stereochemistry; free base)
Compound 5 (free base)
Compound 5a (HCl salt)
Compound 6 (free base)
Compound 6a (HCl salt)
Compound 3 ([α]$_D^{20}$=+8.02° (0.6112 w/v %, DMF); oxalate salt)
Compound 4 ([α]$_D^{20}$=−7.69° (0.5335 w/v %, DMF); oxalate salt)

A mixture of 3-chloro-N,N-dimethyl-1-propanamine* (small amount), Mg (1.45 g, 0.0610 mol) and 1,2-dibromoethane (small amount) in THF (2 ml) was stiffed at 60° C. Subsequently a solution of 3-chloro-N,N-dimethyl-1-propanamine hydrochloride (7.4 g, 0.0610 mol) in THF (50 ml) was added. The reaction mixture was stirred for 1 hour and was then cooled to 5° C. A solution of intermediate 1 (5.5 g, 0.02 mol) in THF (50 ml) was added slowly. The mixture was stiffed at r.t. for 18 hours. An aqueous saturated NH$_4$Cl solution was added and the resulting mixture was extracted with EtOAc. The organic layer was separated, dried (MgSO$_4$), filtered and the solvent was evaporated. The residue (6.3 g) was purified by column chromatography over silica gel (eluent: DCM/MeOH/NH$_4$OH from 96/4/0.3 to 95/5/0.5; 15-40 μm). The desired fractions were collected, yielding 2.35 g of compound 1 (CIS mixture). Compound 1 was purified by column chromatography over silica gel (Chiralpak AD; eluent: heptane/2-propanol/Et$_3$N 97/3/0.1). Two different fractions were collected and the solvent was evaporated. The compound that was eluted first from the column yielded 1.1 g of compound 5 (free base). The compound that was eluted second from the column yielded 1.1 g of compound 6 (free base). Part of compound 5 (1 g) was dissolved in 2-propanol and converted into the HCl-salt with HCl/2-propanol (1.1 eq; 5 N). The precipitate was filtered off and dried. The residue was taken up in MeOH and concentrated. Diethyl ether was added to the residue and the mixture was concentrated, yielding 0.9 g of compound 5a (HCl-salt). Also a part of compound 6 (1 g) was converted into the HCl-salt by the same procedure, yielding 1.0 g of compound 6a (HCl-salt). Compound 5a (0.9 g) was converted into the free base again with H$_2$O/K$_2$CO$_3$/DCM, yielding 0.9 g of the free base. This free base was dissolved in 2-propanone and converted into the ethanedioic acid salt. The precipitate was filtered off and dried. This precipitate was crystallized from 2-propanone/diethyl ether. The product was filtered off and dried to yield 0.8 g of compound 4. Also compound 6a (1.0 g) was converted into its basic form. The residue (0.8 g) was dissolved in 2-propanone and converted into the ethanedioic acid salt. The precipitate was filtered off and dried. This precipitate was crystallized from 2-propanone/diethyl ether. The product was filtered off and dried, yielding 0.82 g of compound 3.

* A saturated solution of NaHCO₃ (205 ml) was slowly added to a suspension of 3-chloro-N,N-dimethyl-1-propanamine hydrochloride (25 g, 0.158 mol, CAS [4584-46-7]) in Et₂O (200 ml). The mixture was stirred at RT for 1 hour, then saturated with K₂CO₃ (solid). The mixture was extracted with Et₂O. The organic layer was dried over MgSO₄ and concentrated at RT under vacuum to afford 15.5 g of 3-chloro-N,N-dimethyl-1-propanamine (yield 75%).

Example B2

Preparation of Compound 7

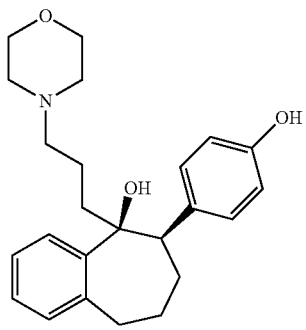 [SMILES: Oc1ccc([C@H]2CCCc3ccccc3[C@]2(O)CCCN2CCOCC2)cc1]

Compound 7 (CIS, Relative Stereochemistry)

A mixture of intermediate 4 (0.4 g, 0.00101 mol), morpholine (0.3 g), Rh(COD)₂BF₄ (0.004 g), Ir(COD)₂BF₄ (0.01 g) and Xantphos (0.024 g) in MeOH/THF (40 ml; 1/1) under CO/H₂ (7/33 atm) atmosphere was reacted in a closed tube for 32 hours at 100° C. Then the mixture was cooled to r.t., filtered, and the filtrate was evaporated (in vacuo). The product was purified by reversed phase HPLC (Shandon Hyperprep® C18 BDS (Base Deactivated Silica) 8 μm, 250 g, I.D. 5 cm). A gradient with 3 mobile phases was applied. Phase A: 90% of a 0.5% NH₄OAc solution in water+10% CH₃CN; phase B: MeOH; phase C: CH₃CN). The desired fractions were collected and the organic solvent was evaporated. The aqueous concentrate was extracted with DCM and washed with an aqueous Na₂CO₃ solution (10%; 2×). The organic layer was separated, dried (MgSO₄), filtered and the solvent was evaporated. The residue was crystallized from DIPE, filtered off and dried. Compound 7 was obtained as a white powder.

Example B3

Preparation of Compound 8

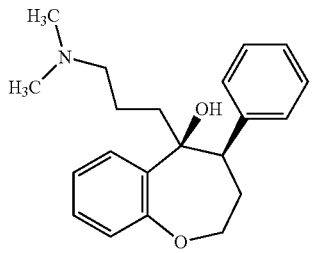 [SMILES: CN(C)CCC[C@@]1(O)c2ccccc2OCC[C@@H]1c1ccccc1]

Compound 8a (CIS, relative stereochemistry; free base)
Compound 8 (CIS, relative stereochemistry; oxalate salt)

A small quantity of 3-chloro-N,N-dimethyl-1-propanamine (obtained as described in B1b), Mg (0.5 g, 0.02 mol) and 1,2-dibromoethane (small amount) in THF (2 ml) was stirred at 60° C. A solution of 3-chloro-N,N-dimethyl-1-propanamine hydrochloride (0.02 mol) in THF (15 ml) was added slowly. The mixture was stirred for 1 hour and was then cooled to 50° C. A solution of intermediate 6 (1.1 g, 0.0070 mol) in THF (10 ml) was added slowly. The mixture was stirred at r.t. overnight. A saturated aqueous NH₄Cl solution was added. The mixture was extracted with EtOAc. The organic layer was separated, dried (MgSO₄), filtered, and the solvent was evaporated. The residue (1.5 g) was purified by column chromatography over Kromasil (eluent: DCM/MeOH/NH₄OH 93/7/0.5; 15-40 μm). The pure fractions were collected and the solvent was evaporated. Yield: 1.1 g of compound 8a (free base; 80%). This fraction was dissolved in 2-propanone and converted into the ethanedioic acid salt (=Oxalate salt). The precipitate was filtered off and dried. Yield: 0.6 g of compound 8.

Example B4

Preparation of Compound 9

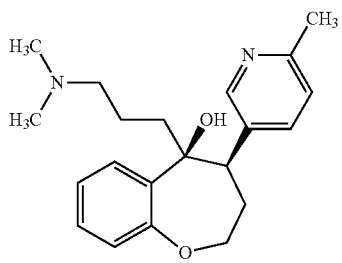

Compound 9 (CIS, relative stereochemistry)

A mixture of intermediate 8 (1.3 g, 0.0046 mol), dimethylamine (2 ml of a MeOH solution), Rh(COD)₂BF₄ (0.004 g), Ir(COD)₂BF₄ (0.010 g) and Xantphos (0.024 g) in MeOH/THF (40 ml; 1/1) under CO/H₂ (7/32 atm) atmosphere was reacted for 32 hours at 100° C. After cooling down, the reaction mixture was filtered and the filtrate was concentrated in vacuo. The residue (1.6 g) was purified by reversed-phase HPLC (Shandon Hyperprep® C18 BDS (Base Deactivated Silica) 8 μm, 250 g, I.D. 5 cm). A gradient with a buffer solution and organic solvents was applied. Subsequently, the product was desalted by HPLC. The product fractions were collected and worked-up. Yield: 0.6 g of compound 9.

Example B5 a) Preparation of Compound 10

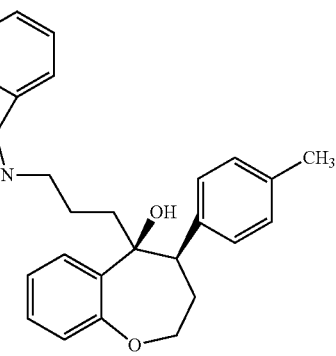

Compound 10 (CIS, relative stereochemistry)

Reaction performed in an autoclave under $N_2$ atmosphere. A mixture of intermediate 10 (1 g, 0.003567 mol), $Rh(COD)_2BF_4$ (0.001448 g), $Ir(COD)_2BF_4$ (0.001766 g), Xantphos (0.020616 g) and N-methylbenzenemethanamine (2 equivalent, 0.864429 g, 0.007133 mol) in MeOH/THF (40 ml, 1/1) was loaded in the autoclave and the autoclave was pressurized to 50 bar $CO/H_2$ (1/3). The mixture was reacted for 32 hours at 100° C. Then the mixture was filtered and the solvent was evaporated. The residue was purified over silica gel (eluent: DCM). The desired fractions were collected and the solvent was evaporated, yielding 0.8 g of compound 10.

b) Preparation of compound 11

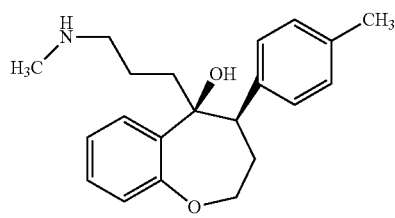

Compound 11a (CIS, relative stereochemistry; free base)
Compound 11 (CIS, relative stereochemistry; oxalte salt)

Pd/C 10% (0.100 g) was suspended in MeOH (50 ml) under $N_2$ flow. Compound 10 (0.9 g, 0.002166 mol) was added and the reaction mixture was stirred at 25° C. under $H_2$ atmosphere until 1 equivalent was absorbed. The catalyst was filtered off over Dicalite. The filtrate was concentrated and the residue (compound 11a; free base) was crystallized as the oxalate salt from diethylether/2-propanol/oxalic acid in 2-propanol. Yield: 0.420 g of compound 11.

Example B6 a) Preparation of Compound 12

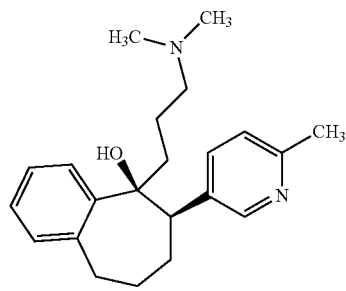 [SMILES: Cc1ccc([C@H]2CCCc3ccccc3[C@]2(O)CCCN(C)C)cn1]

Compound 12 (CIS, relative stereochemistry; oxalate salt)

Reaction performed in an autoclave under $N_2$ atmosphere. A mixture of intermediate 12 (0.935 g, 0.003347 mol), $Rh(COD)_2BF_4$ (0.001359 g), $Ir(COD)_2BF_4$ (0.001658 g), Xantphos (0.019364 g) and dimethylamine (2.0 M solution in MeOH) (2 equivalent) in MeOH/THF (40 ml, 1/1) was loaded in the autoclave and the autoclave was pressurized to 50 bar $CO/H_2$ (1/3). The mixture was reacted for 32 hours at 100° C. The reaction mixture was filtered, the solvent was evaporated and the residue was purified by column chromatography over silicagel (eluent: first DCM; then 5% MeOH/DCM; finally 5% $(MeOH/NH_3)/DCM$). The desired fractions were collected and the solvent was evaporated, yielding an oil which was crystallized as an oxalate. Yield: 0.120 g of compound 12 (8.37%; white hygroscopic solid, oxalate salt).

b) Preparation of Compound 16

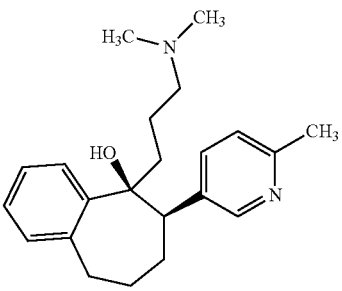 [SMILES: Cc1ccc([C@H]2CCCc3ccccc3[C@]2(O)CCCN(C)C)cn1]

Compound 16 (CIS, relative stereochemistry; 0.2HCl)

A mixture of intermediate 12 (0.1 g, 0.0004 mol), 1 ml of a dimethylamine solution (in MeOH), $Rh(COD)_2BF_4$ (0.002 g), $Ir(COD)_2BF_4$ (0.005 g) and Xantphos (0.012 g) in THF/MeOH (20 ml) under 7 atm CO and 33 atm $H_2$ was stirred for 32 hours at 100° C. Then, the mixture was cooled, filtered and the solvent was evaporated. The residue was purified by reversed phase HPLC (Shandon Hyperprep® C18 BDS (Base Deactivated Silica) 8 μm, 250 g, I.D. 5 cm). A gradient with 3 mobile phases was applied. Phase A: 90% of a 0.5% $NH_4OAc$ solution in water+10% $CH_3CN$; phase B: $CH_3OH$; phase C: $CH_3CN$). The desired fractions were collected. After working-up, the residue was taken up into DIPE and was treated with 2-propanol/HCl. The solid was collected and dried in the oven (hygroscopic), yielding compound 16 as a HCl-salt (0.2HCl)

Example B7

Preparation of Compound 13

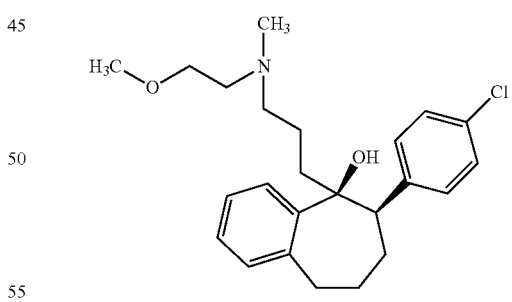

Compound 13 (CIS, relative stereochemistry; .HCl)

A mixture of intermediate 2 (0.4 g, 0.0013 mol), 2-methoxy-N-methylethanamine (0.3 g, 0.00337 mol), $Rh(COD)_2BF_4$ (0.004 g), $Ir(COD)_2BF_4$ (0.010 g) and Xantphos (0.024 g) in MeOH/THF (40 ml; 1/1) under $CO/H_2$ (7/33 atm) atmosphere was reacted in a closed tube for 32 hours at 100° C. After cooling to r.t., the solution was filtered and the filtrate was evaporated. The residue was purified by reversed-phase HPLC (Shandon Hyperprep® C18 BDS (Base Deactivated Silica) 8 μm, 250 g, I.D. 5 cm). A gradient with 3 mobile phases was applied. Phase A: a 0.25% $NH_4HCO_3$ solution in water; phase B: CH₃OH; phase C: CH₃CN). The desired fractions were collected and worked-up. The product was dissolved in DIPE and HCl/2-propanol was added to obtain compound 13 as a HCl-salt.

Example B8

Preparation of Compound 14

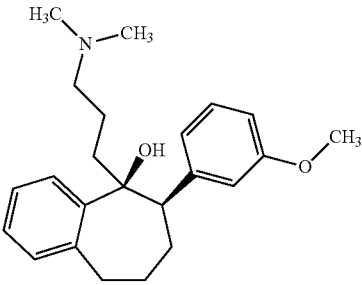 [SMILES: COc1cccc([C@H]2CCCc3ccccc3[C@]2(O)CCCN(C)C)c1]

Compound 14a (CIS, relative stereochemistry; free base)
Compound 14 (CIS, relative stereochemistry; oxalate salt)

A small amount of 3-chloro-N,N-dimethyl-1-propanamine (obtained as described in B1b), Mg (0.5 g, 0.02 mol) and 1,2-dibromoethane (small amount) in THF (2 ml) was heated at 60° C. When the reaction started, a solution of 3-chloro-N,N-dimethyl-1-propanamine hydrochloride (2.5 g, 0.02 mol) in THF (25 ml) was added slowly. The reaction mixture was stirred for 1 hour at 60° C. and was then cooled to 5° C. A solution of intermediate 13 (1.8 g, 0.0070 mol) in THF (25 ml) was added slowly. The mixture was stirred overnight at r.t. NH₄Cl (10%) was added and the mixture was filtered over Celite. The filtrate was extracted with EtOAc. The organic layer was separated, dried (MgSO₄), filtered and the solvent was evaporated. The residue (2.2 g) was purified by column chromatography over silica gel (eluent: DCM/MeOH/NH₄OH 95/5/0.2; 15-40 µm). The pure fractions were collected and the solvent was evaporated, yielding compound 14a (free base). 1 g of compound 14a was converted into the oxalate salt, yielding 0.615 g of compound 14.

Example B9

Preparation of Compound 15

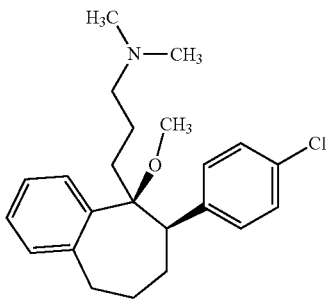 [SMILES: CO[C@]1(CCCN(C)C)c2ccccc2CCC[C@@H]1c1ccc(Cl)cc1]

Compound 15 (CIS, relative stereochemistry)
A mixture of intermediate 14 (0.5 g, 0.0016 mol), a dimethylamine solution (1 ml; in MeOH), Rh(COD)₂BF₄ (0.004 g), Ir(COD)₂BF₄ (0.010 g) and Xantphos (0.024 g) in THF/ MeOH (40 ml; 1/1) was stirred for 32 hours at 100° C. under CO/H₂ atmosphere (7 atm/32 atm). After cooling, the reaction mixture was filtered and concentrated in vacuo. The residue was purified twice by column chromatography over silica gel (eluent: DCM/MeOH 95/5). The product fractions were collected and the solvent was evaporated. Yield: 0.0685 g of compound 15.

Example B10

Preparation of Compound 17

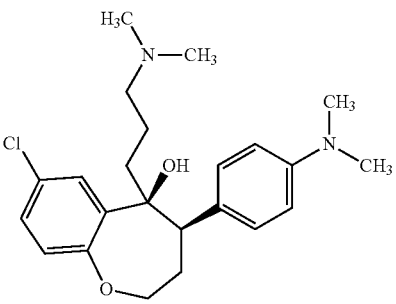 [SMILES: CN(C)CCC[C@@]1(O)c2cc(Cl)ccc2OCC[C@@H]1c1ccc(N(C)C)cc1]

Compound 17 (CIS, relative stereochemistry)
Reaction is performed in an autoclave under N₂ atmosphere. A mixture of intermediate 16 (0.003347 mol), Rh(COD)₂BF₄ (0.001359 g), Ir(COD)₂BF₄ (0.001658 g), Xantphos (0.0000334 mol) and dimethylamine (2.0 M solution in MeOH) (2 equivalent) in MeOH/THF (40 ml, 1/1) is loaded in the autoclave and the autoclave is pressurized to 50 bar CO/H₂ (1/3). The mixture is reacted for 32 hours at 100° C. The reaction mixture is filtered, the solvent is evaporated and the residue is purified by column chromatography over silicagel. Yield: Compound 17.

Example B11

Preparation of Compound 18

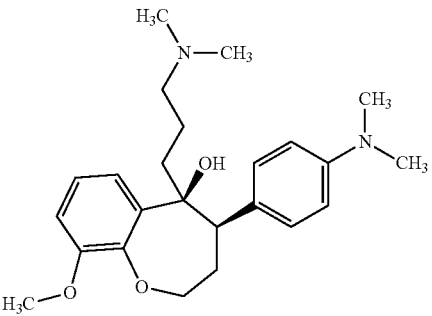

Compound 18 (CIS, relative stereochemistry)
Reaction is performed in an autoclave under N₂ atmosphere. A mixture of intermediate 18 (0.003347 mol), Rh(COD)₂BF₄ (0.001359 g), Ir(COD)₂BF₄ (0.001658 g), Xantphos (0.0000334 mol) and dimethylamine (2.0 M solution in MeOH) (2 equivalent) in MeOH/THF (40 ml, 1/1) is loaded in the autoclave and the autoclave is pressurized to 50 bar CO/H₂ (1/3). The mixture is reacted for 32 hours at 100° C. The reaction mixture is filtered, the solvent is evaporated and the residue is purified by column chromatography over silicagel. Yield: Compound 18.

The following compounds of formula (I), as depicted in Tables 4 to 7, were prepared by analogy to the above examples (Ex. No.) using alternative starting materials as appropriate.

TABLE 4

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 19 | B5b | ---H | ---NH---CH₃ | phenyl | oxalate salt |
| 20 | B10 | ---H | ---N(CH₃)₂ | phenyl | |
| 106 | B10 | ---H | ---N(CH₃)₂ | phenyl | oxalate salt |
| 21 | B2 | ---H | pyrrolidinyl | phenyl | oxalate salt |
| 22 | B5b | ---H | ---NH---CH₃ | 3-methylphenyl | oxalate salt |
| 23 | B7 | ---H | ---N(CH₃)CH₂CH₂OCH₃ | 3-methylphenyl | oxalate salt |
| 24 | B5a | ---H | ---N(CH₃)CH₂-phenyl | 3-methylphenyl | oxalate salt |
| 25 | B2 | ---H | morpholinyl | 3-methylphenyl | oxalate salt |

TABLE 4-continued

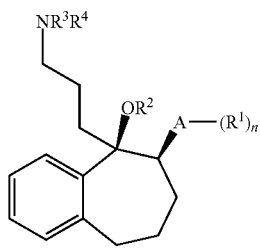

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 26 | B2 | ---H | N-methylpiperazine-N'-acetyl | 3-methylphenyl | |
| 27 | B5b | ---H | NHCH₃ | 4-methylphenyl | oxalate salt |
| 28 | B5 | ---H | pyrrolidinyl | 4-methylphenyl | |
| 29 | B6 | ---H | ---N(CH₃)₂ | 4-methylphenyl | oxalate salt |
| 30 | B7 | ---H | N(CH₃)CH₂CH₂OCH₃ | 4-methylphenyl | oxalate salt |
| 31 | B6 | ---H | N(CH₂CH₃)₂ | 4-methylphenyl | oxalate salt |
| 32 | B2 | ---H | piperidinyl | 4-methylphenyl | oxalate salt |
| 33 | B2 | ---H | 4-methylpiperazinyl | 4-methylphenyl | oxalate salt |
| 34 | B2 | ---H | 4-acetylpiperazinyl | 4-methylphenyl | |
| 35 | B2 | ---H | ---N(CH₃)₂ | 4-hydroxyphenyl | |

TABLE 4-continued (±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 36 | B2 | ---H | N(CH₂CH₃)₂ | 4-hydroxyphenyl | |
| 37 | B7 | ---H | N(CH₃)CH₂CH₂OCH₃ | 4-hydroxyphenyl | oxalate salt |
| 7 | B2 | ---H | morpholinyl | 4-hydroxyphenyl | |
| 38 | B6 | ---H | ---N(CH₃)₂ | 4-bromophenyl | oxalate salt |
| 39 | B5b | ---H | NHCH₃ | 3-chlorophenyl | oxalate salt |
| 40 | B6 | ---H | ---N(CH₃)₂ | 3-chlorophenyl | oxalate salt |
| 41 | B6 | ---H | N(CH₂CH₃)₂ | 3-chlorophenyl | oxalate salt |
| 42 | B7 | ---H | N(CH₃)CH₂CH₂OCH₃ | 3-chlorophenyl | oxalate salt |
| 43 | B5b | ---H | NHCH₃ | 4-chlorophenyl | |

TABLE 4-continued

[Structure: bicyclic benzo-fused 7-membered ring with NR³R⁴-propyl, OR², and A—(R¹)ₙ substituents]

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 44 | B5b | ---H | ---NH-CH₂-CH₃ | 4-Cl-phenyl | |
| 45 | B5b | ---H | ---NH-CH(CH₃)₂ | 4-Cl-phenyl | |
| 1 | B1.a-1B1.b | ---H | ---N(CH₃)₂ | 4-Cl-phenyl | |
| 2 | B1.a-2 | ---H | ---N(CH₃)₂ | 4-Cl-phenyl | oxalate salt |
| 15 | B9 | ---CH₃ | ---N(CH₃)₂ | 4-Cl-phenyl | |
| 46 | B6 | ---H | ---N(CH₂CH₃)₂ | 4-Cl-phenyl | HCl salt |
| 13 | B7 | ---H | ---N(CH₃)CH₂CH₂OCH₃ | 4-Cl-phenyl | HCl salt |
| 47 | B5a | ---H | ---N(CH₃)CH₂-phenyl | 4-Cl-phenyl | HCl salt |
| 48 | B2 | ---H | pyrrolidin-1-yl | 4-Cl-phenyl | oxalate salt |
| 49 | B2 | ---H | 3-hydroxypyrrolidin-1-yl | 4-Cl-phenyl | oxalate salt |

TABLE 4-continued

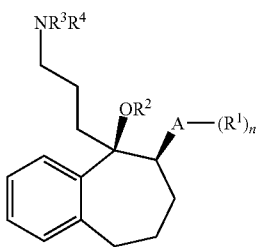

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 50 | B2 | ---H | piperidin-1-yl | 4-Cl-phenyl | oxalate salt |
| 51 | B2 | ---H | piperazin-1-yl | 4-Cl-phenyl | oxalate salt |
| 52 | B6 | ---H | ---N(CH₃)₂ | 4-F-phenyl | oxalate salt |
| 53 | B6 | ---H | N(CH₂CH₃)₂ | 4-F-phenyl | oxalate salt |
| 54 | B7 | ---H | N(CH₃)(CH₂CH₂OCH₃) | 4-F-phenyl | oxalate salt |
| 55 | B2 | ---H | 4-methylpiperazin-1-yl | 4-F-phenyl | oxalate salt |
| 56 | B6 | ---H | ---N(CH₃)₂ | 2,4-diF-phenyl | oxalate salt |
| 57 | B6 | ---H | N(CH₂CH₃)₂ | 2,4-diF-phenyl | oxalate salt |
| 58 | B7 | ---H | N(CH₃)(CH₂CH₂OCH₃) | 2,4-diF-phenyl | oxalate salt |

TABLE 4-continued

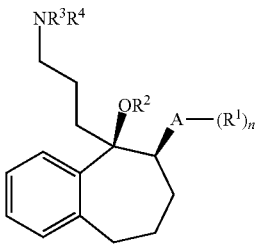

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 59 | B2 | ---H | piperidine | 2,4-difluorophenyl | oxalate salt |
| 60 | B2 | ---H | 4-acetylpiperazine | 2,4-difluorophenyl | oxalate salt |
| 14 | B8 | ---H | ---N(CH₃)₂ | 3-methoxyphenyl | oxalate salt |
| 14a | B8 | ---H | ---N(CH₃)₂ | 3-methoxyphenyl | |
| 61 | B6 | ---H | N(CH₂CH₃)₂ | 3-methoxyphenyl | HCl salt |
| 62 | B5a | ---H | N(CH₃)(CH₂C₆H₅) | 3-methoxyphenyl | HCl salt |
| 63 | B2 | ---H | 4-acetylpiperazine | 3-methoxyphenyl | oxalate salt |
| 64 | B5b | ---H | ---NH₂ | 4-methoxyphenyl | oxalate salt |
| 65 | B5b | ---H | ---NHCH₃ | 4-methoxyphenyl | oxalate salt |
| 66 | B6 | ---H | ---N(CH₃)₂ | 4-methoxyphenyl | oxalate salt |

TABLE 4-continued

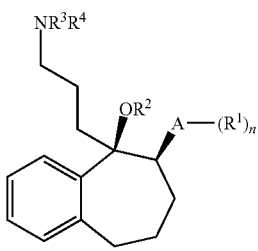

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 67 | B6 | ---H | N(CH₂CH₃)₂ | 4-methoxyphenyl | oxalate salt |
| 68 | B5b | ---H | NH-CH₂-phenyl | 4-methoxyphenyl | |
| 69 | B5a | ---H | N(CH₃)-CH₂-phenyl | 4-methoxyphenyl | |
| 70 | B7 | ---H | N(CH₃)CH₂CH₂OCH₃ | 4-methoxyphenyl | oxalate salt |
| 71 | B2 | ---H | 4-acetylpiperazin-1-yl | 4-methoxyphenyl | |
| 72 | B6 | ---H | ---N(CH₃)₂ | 2-chloro-3-methoxyphenyl | |
| 73 | B2 | ---H | 3-hydroxypyrrolidin-1-yl | 2-chloro-3-methoxyphenyl | |
| 74 | B6 | ---H | N(CH₂CH₃)₂ | 2-chloro-3-methoxyphenyl | oxalate salt |
| 75 | B7 | ---H | N(CH₃)CH₂CH₂OCH₃ | 2-chloro-3-methoxyphenyl | oxalate salt |

TABLE 4-continued
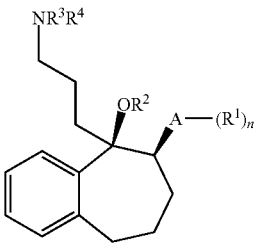
(±)-CIS (5S, 6R; 5R, 6S) (relative stereochemistry)
| Co. No. | Ex. No. | R² | NR³R⁴ | A—(R¹)ₙ | Salt |
|---|---|---|---|---|---|
| 76 | B5b | ---H |  | 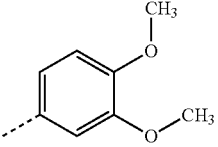 | |
| 77 | B6 | ---H | ---N(CH₃)₂ | 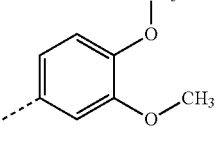 | oxalate salt |
| 78 | B6 | ---H | 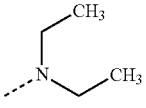 | 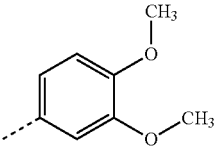 | oxalate salt |
| 79 | B7 | ---H | 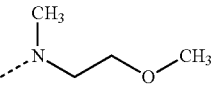 | 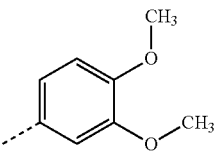 | oxalate salt |
| 80 | B5a | ---H | 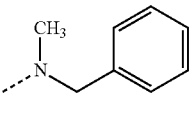 | 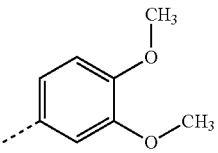 | |
| 16 | B6.b | ---H | ---N(CH₃)₂ | 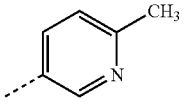 | •2HCl |
| 12 | B6.a | ---H | ---N(CH₃)₂ | 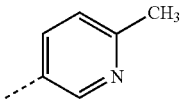 | oxalate salt |
| 81 | B6a | ---H | ---N(CH₃)₂ | 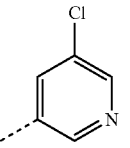 | •2HCl |

TABLE 4-continued

[Structure: benzo-fused seven-membered ring with substituents NR³R⁴ (via propyl chain), OR², and A—(R¹)ₙ]

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 82 | B5b | ---H | ---NH-CH(CH₃)₂ | 3-chloropyridin-5-yl | ·2HCl |
| 83 | B6a | ---H | ---N(CH₃)₂ | 3-methoxypyridin-5-yl | |
| 84 | B6a | ---H | ---N(CH₃)₂ | pyrimidin-5-yl | |
| 85 | B6a | ---H | ---N(CH₃)₂ | quinolin-3-yl | |
| 86 | B5b | ---H | ---NH-CH(CH₃)₂ | quinolin-3-yl | |
| 87 | B5a | ---H | ---N(CH₃)(CH₂-phenyl) | quinolin-3-yl | |
| 88 | B6 | ---H | ---N(CH₃)₂ | benzo[1,3]dioxol-5-yl | oxalate salt |
| 89 | B6 | ---H | ---N(CH₂CH₃)₂ | benzo[1,3]dioxol-5-yl | oxalate salt |

TABLE 4-continued

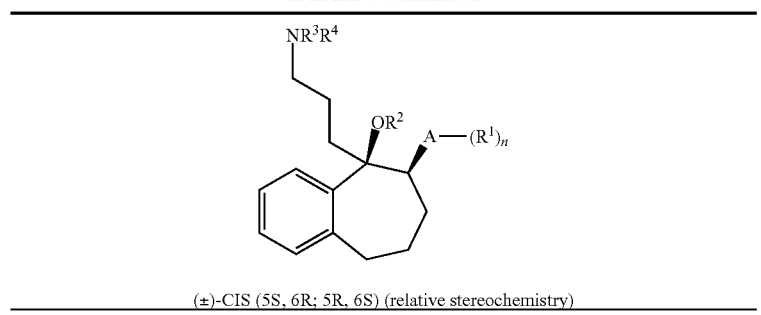

(±)-CIS (5S, 6R; 5R, 6S) (relative stereochemistry)

| Co. No. | Ex. No. | R² | NR³R⁴ | A—(R¹)ₙ | Salt |
|---|---|---|---|---|---|
| 90 | B7 | ---H | —N(CH₃)—CH₂CH₂—O—CH₃ | benzo[1,3]dioxole | oxalate salt |
| 91 | B2 | ---H | 3-hydroxypyrrolidin-1-yl | benzo[1,3]dioxole | |

TABLE 5

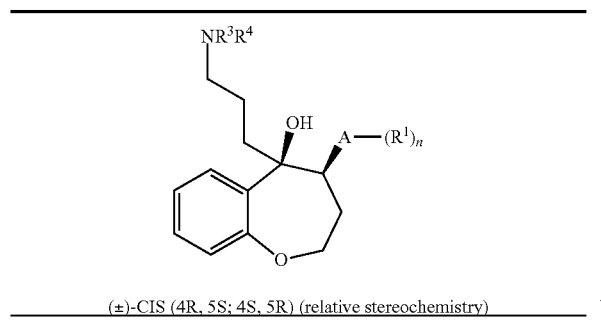

(±)-CIS (4R, 5S; 4S, 5R) (relative stereochemistry)

| Co. No. | Ex. No. | NR³R⁴ | A—(R¹)ₙ | Salt |
|---|---|---|---|---|
| 8 | B3 | ---N(CH₃)₂ | phenyl | oxalate salt |
| 8a | B3 | ---N(CH₃)₂ | phenyl | |
| 11 | B5.b | ---NH—CH₃ | 4-CH₃-phenyl | oxalate salt |
| 11a | B5.b | ---NH—CH₃ | 4-CH₃-phenyl | |
| 92 | B3 | ---N(CH₃)₂ | 4-CH₃-phenyl | oxalate salt |

TABLE 5-continued

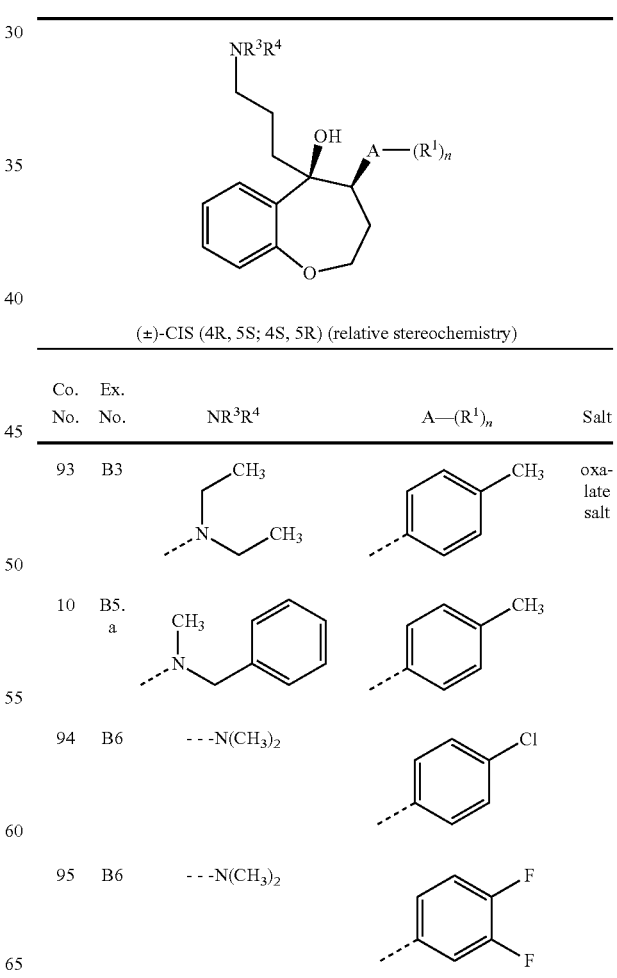

(±)-CIS (4R, 5S; 4S, 5R) (relative stereochemistry)

| Co. No. | Ex. No. | NR³R⁴ | A—(R¹)ₙ | Salt |
|---|---|---|---|---|
| 93 | B3 | —N(CH₂CH₃)₂ | 4-CH₃-phenyl | oxalate salt |
| 10 | B5.a | —N(CH₃)(CH₂-phenyl) | 4-CH₃-phenyl | |
| 94 | B6 | ---N(CH₃)₂ | 4-Cl-phenyl | |
| 95 | B6 | ---N(CH₃)₂ | 3,4-diF-phenyl | |

TABLE 5-continued

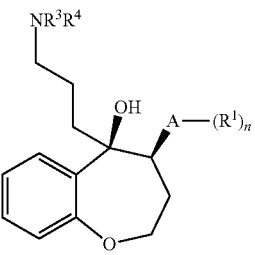

(±)-CIS (4R, 5S; 4S, 5R) (relative stereochemistry)

| Co. No. | Ex. No. | NR³R⁴ | A—(R¹)ₙ | Salt |
|---|---|---|---|---|
| 96 | B6 | ---N(CH₃)₂ | 2-methoxyphenyl | |
| 97 | B6 | ---N(CH₃)₂ | 4-chloro-3-methoxyphenyl | oxalate salt |
| 98 | B6 | N(CH₂CH₃)₂ | 4-chloro-3-methoxyphenyl | oxalate salt |
| 9 | B4 | ---N(CH₃)₂ | 6-methylpyridin-3-yl | |

TABLE 5-continued

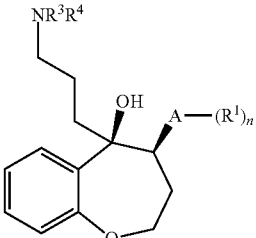

(±)-CIS (4R, 5S; 4S, 5R) (relative stereochemistry)

| Co. No. | Ex. No. | NR³R⁴ | A—(R¹)ₙ | Salt |
|---|---|---|---|---|
| 99 | B4 | ---N(CH₃)₂ | 6-methylpyridin-3-yl | oxalate salt |
| 100 | B6 | ---N(CH₃)₂ | 5-methoxypyridin-3-yl | |
| 101 | B6 | N(CH₂CH₃)₂ | 5-methoxypyridin-3-yl | |
| 102 | B6 | ---N(CH₃)₂ | 6-methoxypyridin-3-yl | oxalate salt |
| 103 | B6 | N(CH₂CH₃)₂ | 6-methoxypyridin-3-yl | oxalate salt |

TABLE 6

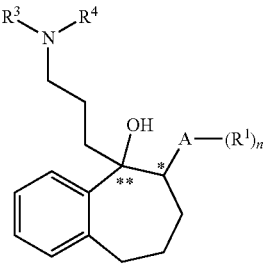

pure enantiomer (relative stereochemistry)

| Co. No. | Ex. No. | * | ** | R³ | R⁴ | A—(R¹)ₙ | Salt |
|---|---|---|---|---|---|---|---|
| 104 | B1.b | R (rel) | S (rel) | ---CH₃ | ---CH₃ | phenyl | oxalate salt |
| 105 | B1.b | S (rel) | R (rel) | ---CH₃ | ---CH₃ | phenyl | oxalate salt |

TABLE 6-continued
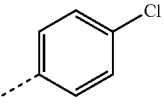
pure enantiomer (relative stereochemistry)
| Co. No. | Ex. No. | * | ** | R³ | R⁴ | A—(R¹)ₙ | Salt |
|---|---|---|---|---|---|---|---|
| 5 | B1.b | R (rel) | S (rel) | ---CH₃ | ---CH₃ | 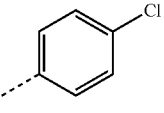 | |
| 5a | B1.b | R (rel) | S (rel) | ---CH₃ | ---CH₃ | 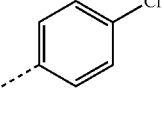 | HCl salt |
| 4 | B1.a-1B1.a-2B1.b | R (rel) | S (rel) | ---CH₃ | ---CH₃ | | oxalate salt |
| 6 | B1.b | S (rel) | R (rel) | ---CH₃ | ---CH₃ | 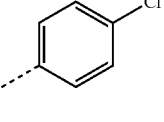 | |
| 6a | B1.b | S (rel) | R (rel) | ---CH₃ | ---CH₃ | 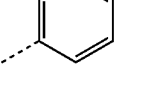 | HCl salt |
| 3 | B1.a-1B1.a-2B1.b | S (rel) | R (rel) | ---CH₃ | ---CH₃ | 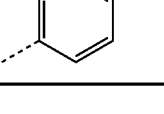 | oxalate salt |

TABLE 7

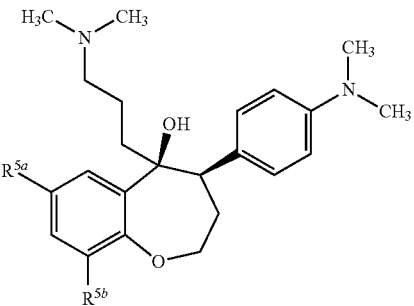

(±)-CIS (4R, 5S; 4S, 5R)
(relative stereochemistry)

| Co. No. | Ex. No. | $R^{5a}$ | $R^{5b}$ |
|---|---|---|---|
| 17 | B10 | ---Cl | ---H |
| 18 | B11 | ---H | ---OCH$_3$ |

C. Analytical Part

Melting Points

Method (a): melting points (m.p.) were determined with a DSC823e (Mettler-Toledo). Melting points were measured with a temperature gradient of 30° C./minute. The reported values are peak values.

Method (b): melting points were obtained with a Kofler hot bench, consisting of a heated plate with linear temperature gradient, a sliding pointer and a temperature scale in degrees Celsius. The bench was calibrated with standard substances.

TABLE 8

Melting points

| Co. Nr. | m.p. (° C.) | Co. Nr. | m.p. (° C.) |
|---|---|---|---|
| 4 | 168.9 (a) | 46 | 189.8 (a) |
| 66 | 100 (b) | 71 | 165.1 (a) |
| 104 | 210 (b) | int 33 | 121.3 (a) |
| 105 | 178 (b) | int 30 | 141.2 (a) |
| 8 | 136 (b) | 7 | 177.1 (a) |
| 21 | 202 (b) | 36 | 141.4 (a) |
| 14 | 108 (b) | 2 | 141.8 (a) |
| 63 | 153.0 (a) | 84 | 134.3 (a) |
| 3 | 168.7 (a) | 41 | 160.3 (a) |
| 70 | 132.2 (a) | 27 | 235.8 (a) |
| 25 | 204.8 (a) | 19 | 129.0 (a) |
| 59 | 211.5 (a) | 67 | 153.0 (a) |
| 58 | 140.0 (a) | 31 | 158.6 (a) |
| 34 | 216.2 (a) | 29 | 161.8 (a) |
| 30 | 144.9 (a) | 22 | 137.4 (a) |
| 33 | 219.0 (a) | int 32 | 143.6 (a) |
| 50 | 201.1 (a) | int 34 | 179.8 (a) |
| 37 | 191.1 (a) | 85 | 150.3 (a) |
| 57 | 160.3 (a) | 86 | 115.2 (a) |
| 65 | 134.3 (a) | 28 | 139.8 (a) |
| 48 | 236.2 (a) | int 31 | 153.4 (a) |

LCMS

LCMS General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS General Procedure C

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters—for LCMS methods 7 and 8), and 3.15 kV at 110° C. on the ZQ™ (simple quadrupole Zspray™ mass spectrometer from Waters—for LCMS methods 9 and 10). $N_2$ was used as the nebulizer gas. Data acquisition was performed with a Waters-Micromass MassLynx-Openlynx data system.

LCMS—Method 1

In addition to general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Method 2

In addition to general procedure A: Reversed phase HPLC was carried out on an Atlantis C18 column (3.5 μm, 4.6×100 mm) (3.5 μm, 4.6×100 mm) with a flow rate of 1.6 ml/min Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 μl was used. Cone voltage was 10 V for positive ionization mode and 20 V for negative ionization mode.

LCMS—Method 3

In addition to general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Method 4

In addition to general procedure A: Column heater was set at 45° C. Reversed phase HPLC was carried out on an Xterra MS C18 column (3.5 μm, 4.6×100 mm) with a flow rate of 1.6 ml/min. Three mobile phases (mobile phase A: 0.1% formic acid in $H_2O$/methanol 95/5; mobile phase B: acetonitrile; mobile phase C: methanol) were employed to run a gradient condition from 100% A to 1% A, 49% B and 50% C in 7 minutes and hold these conditions for 1 minute. An injection volume of 10 μl was used. Cone voltage was 10 V for positive ionization mode.

LCMS—Method 5

In addition to general procedure B: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS—Method 6

In addition to general procedure A: Column heater was set at 45° C. Reversed phase HPLC was carried out on an Atlantis C18 column (3.5 μm, 4.6×100 mm) with a flow rate of 1.6 ml/min Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 9 minutes and hold these conditions for 3 minutes. An injection volume of 10 μl was used.

LCMS—Method 7

In addition to general procedure C: Reversed phase HPLC was carried out on a Kromasil C18 column (5 μm, 4.6×150 mm) with a flow rate of 1.0 ml/min. Three mobile phases (mobile phase A: 100% 7 mM ammonium acetate; mobile phase B: 100% acetonitrile; mobile phase C, 0.2% formic acid+99.8% ultra-pure Water) were employed to run a gradient condition from 30% A, 40% B and 30% C (hold for 1 minute) to 100% B in 4 minutes, 100% B for 5 minutes and reequilibrated with initial conditions for 3 minutes. An injection volume of 5 μl was used. Cone voltage was 20 V for positive ionization mode. Mass spectra were acquired by scanning from 100 to 900 in 0.8 seconds using an interscan delay of 0.08 seconds.

LCMS—Method 8

In addition to general procedure C: Reversed phase HPLC was carried out on a Xterra-MS C18 column (5 μm, 4.6×150 mm) with a flow rate of 1.0 ml/min Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 μl was used. Cone voltage was 20 V for positive ionization mode. Mass spectra were acquired by scanning from 100 to 900 in 0.8 seconds using an interscan delay of 0.08 seconds.

LCMS—Method 9

In addition to general procedure C: Reversed phase HPLC was carried out on a Xterra-MS C18 column (3.5 μm, 4.6×100 mm) with a flow rate of 0.8 ml/min Two mobile phases (mobile phase A: 100% 7 mM ammonium acetate; mobile phase B: 100% acetonitrile; were employed to run a gradient condition from 80% A, 20% B (hold for 0.5 minute) to 10% A, 90% B in 4.5 minutes, hold at 10% A and 90% B for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

LCMS—Method 10

In addition to general procedure C: Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

TABLE 9

Analytical LCMS data: $R_t$ is retention time in minutes; $[MH]^+$ means the protonated mass of the compound; LCMS method

| Co. Nr. | $R_t$ | $[MH]^+$ | LCMS Method |
|---|---|---|---|
| 1 | 4.46 | 358 | 7 |
| 2 | 1.08 | 358 | 5 |
| 3 | 1.10 | 358 | 5 |
| 4 | 1.11 | 358 | 5 |
| int 4 | 1.67 | 395 | 5 |
| 5 | 4.27 | 358 | 7 |
| 6 | 4.40 | 358 | 7 |
| 7 | 5.43 | 382 | 1 |
| 8 | 7.27 | 326 | 8 |
| 10 | 1.08 | 416 | 5 |
| 11 | 0.99 | 326 | 5 |
| 12 | 0.48 | 339 | 5 |
| 13 | 6.04 | 402 | 1 |
| 14 | 7.87 | 354 | 8 |
| 15 | 1.16 | 372 | 5 |
| 16 | 0.53 | 339 | 5 |
| 19 | 4.82 | 310 | 1 |
| int 20 | 1.49 | 279 | 5 |
| 20 | 4.98 | 324 | 1 |
| 21 | 6.03 | 350 | 9 |
| int 21 | 1.49 | 279 | 5 |
| 22 | 5.23 | 324 | 1 |
| 23 | 5.81 | 382 | 1 |
| 24 | 7.02 | 414 | 1 |
| 25 | 6.59 | 380 | 1 |
| 26 | 6.40 | 421 | 1 |
| int 27 | 1.43 | 295 | 5 |
| 27 | 5.22 | 324 | 1 |
| 28 | 1.09 | 364 | 5 |
| 29 | 5.36 | 338 | 1 |
| int 30 | 0.90 | 280 | 5 |
| 30 | 5.86 | 382 | 1 |
| 31 | 5.49 | 366 | 1 |
| int 31 | 8.78 | 300 | 2 |
| 32 | 5.73 | 378 | 1 |

TABLE 9-continued

Analytical LCMS data: $R_t$ is retention time in minutes; [MH]$^+$ means the protonated mass of the compound; LCMS method

| Co. Nr. | $R_t$ | [MH]$^+$ | LCMS Method |
|---|---|---|---|
| int 32 | 1.04 | 296 | 5 |
| int 33 | 1.15 | 267 | 5 |
| 33 | 6.17 | 393 | 1 |
| 34 | 6.38 | 421 | 1 |
| int 34 | 7.86 | 316 | 2 |
| 35 | 4.05 | 340 | 1 |
| 36 | 4.29 | 368 | 1 |
| 37 | 4.51 | 384 | 1 |
| 38 | 4.67 | 402 | 4 |
| 39 | 5.20 | 344 | 1 |
| 40 | 5.41 | 358 | 1 |
| 41 | 5.52 | 386 | 1 |
| 42 | 5.89 | 402 | 1 |
| 43 | 5.35 | 344 | 1 |
| 44 | 1.10 | 358 | 5 |
| 45 | 7.43 | 372 | 6 |
| 46 | 5.65 | 386 | 1 |
| 47 | 7.11 | 434 | 1 |
| 48 | 5.58 | 384 | 1 |
| 49 | 5.49 | 400 | 1 |
| 50 | 5.88 | 398 | 1 |
| 51 | 5.70 | 399 | 1 |
| 52 | 5.12 | 342 | 1 |
| 53 | 5.24 | 370 | 1 |
| 54 | 5.58 | 386 | 1 |
| 55 | 5.86 | 397 | 1 |
| 56 | 5.25 | 360 | 1 |
| 57 | 5.40 | 388 | 1 |
| 58 | 5.79 | 404 | 1 |
| 59 | 5.65 | 400 | 1 |
| 60 | 6.24 | 443 | 1 |
| 61 | 5.08 | 382 | 1 |
| 62 | 6.70 | 430 | 1 |
| 64 | 1.01 | 326 | 5 |
| 65 | 4.83 | 340 | 1 |
| 66 | 4.03 | 354 | 10 |
| 67 | 5.11 | 382 | 1 |
| 68 | 1.16 | 416 | 5 |
| 69 | 1.09 | 430 | 5 |
| 70 | 5.44 | 398 | 1 |
| 71 | 6.03 | 437 | 1 |
| 72 | 1.06 | 388 | 5 |
| 73 | 1.06 | 430 | 5 |
| 74 | 1.08 | 416 | 5 |
| 75 | 1.08 | 432 | 5 |
| 76 | 0.94 | 370 | 5 |
| 77 | 0.93 | 384 | 5 |
| 78 | 0.96 | 412 | 5 |
| 79 | 0.96 | 428 | 5 |
| 81 | 0.94 | 359 | 5 |
| 82 | 0.98 | 373 | 5 |
| 83 | 0.65 | 355 | 5 |
| 84 | 0.70 | 326 | 5 |
| 85 | 4.92 | 375 | 1 |
| 86 | 4.94 | 389 | 1 |
| 87 | 0.99 | 451 | 5 |
| 88 | 0.98 | 368 | 5 |
| 89 | 1.01 | 396 | 5 |
| 90 | 1.00 | 412 | 5 |
| 91 | 0.98 | 410 | 5 |
| 92 | 0.98 | 340 | 5 |
| 93 | 5.03 | 368 | 1 |
| 94 | 1.01 | 360 | 5 |
| 95 | 0.96 | 362 | 5 |
| 96 | 0.94 | 356 | 5 |
| 97 | 4.78 | 390 | 3 |
| 98 | 6.72 | 418 | 6 |
| 99 | 0.41 | 341 | 5 |
| 100 | 3.59 | 357 | 6 |
| 101 | 0.63 | 385 | 5 |
| 102 | 0.81 | 357 | 5 |
| 103 | 0.86 | 385 | 5 |
| 104 | 7.91 | 324 | 8 |
| 105 | 7.98 | 324 | 8 |

Optical Rotation

The optical rotation was measured using a Perkin Elmer 341 polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned.

TABLE 10

Optical rotation data

| Co. Nr. | $[\alpha]_D^{20}$ | concentration | solvent |
|---|---|---|---|
| 3 | +8.02° | 0.6112 w/v % | DMF |
| 105 | +10.76° | 0.6320 w/v % | DMF |
| 104 | −11.02° | 0.5265 w/v % | DMF |
| 4 | −7.69° | 0.5335 w/v % | DMF |

D. Pharmacolotical Example

Ghrelin-Agonism in HEK293 Cells

One day before the experiment, HEK293 cells, permanently transfected with the gene sequence for expression of the GHS1A-receptor, were seeded in poly-D-Lysine coated 96-well plates with clear bottom, and allowed to grow to ~75% of confluence on the next day.

Then, cells were incubated with the calcium-sensitive intracellular fluorescent probe fluo-4 or Kit-3 for 1 h at 37° C. Fluorescence representing free intracellular calcium in the cells was measured in a FLIPR-system (excitation at 488 nm, emission >520 nm). Test compounds were added to each well at the desired concentration and the fluorescence signal was simultaneously recorded in all wells. Release of intracellular calcium triggered by activation of the receptors upon addition of the test compound was measured as the fluorescence emitted from the complex of calcium and the fluorescent probe. The drug effect on fluorescence intensity was expressed relative to the maximal fluorescence intensity measured in cells exposed to the calcium-ionophore ionomycin. Curve-fitting of concentration-response data was used to determine $pEC_{50}$-values for test compounds ($pEC_{50}=-\log EC_{50}$; $EC_{50}$ being the effective dose in M and defined as the concentration of the test compound resulting in an effect size that is 50% of the maximal effect size (=100%) that can be reached. Table 11 below discloses $pEC_{50}$ values. As a positive control, the reference compound GHRP-6 concentration-dependently increased fluorescence with an average $pEC_{50}$-value of 9.0±0.1 (mean±SEM, n=19).

TABLE 11 pEC$_{50}$ values

| Co. No. | pEC$_{50}$ | Co. No. | pEC$_{50}$ | Co. No. | pEC$_{50}$ |
|---|---|---|---|---|---|
| 5 | 6.0 | 58 | 6.9 | 98 | 8.0 |
| 4 | 5.5 | 34 | 5.5 | 85 | 7.0 |
| 6 | 8.0 | 30 | 7.1 | 87 | 5.8 |
| 66 | 6.6 | 33 | 5.5 | 86 | 6.2 |
| 104 | 5.7 | 50 | 6.1 | 10 | 6.6 |
| 105 | 7.8 | 51 | 5.8 | 101 | 5.7 |
| 8 | 6.5 | 76 | 5.8 | 81 | 7.3 |
| 21 | 7.1 | 37 | 5.7 | 82 | 6.6 |
| 14 | 7.9 | 57 | 7.5 | 11 | 6.4 |
| 63 | <5 | 65 | 6.1 | 100 | 5.4 |
| 13 | 6.6 | 32 | 6.0 | 68 | <4.5 |
| 46 | 6.7 | 48 | 7.5 | 28 | 6.8 |
| 47 | 5.3 | 41 | 8.1 | 44 | 6.3 |
| 71 | <5 | 27 | 7.1 | 45 | 6.1 |
| 69 | <5 | 19 | 6.7 | 64 | 4.6 |
| 16 | 6.6 | 67 | 6.8 | 12 | 6.6 |
| 24 | 5.4 | 23 | 7.5 | 96 | 5.7 |
| 62 | 5.6 | 60 | 5.4 | 102 | 5.1 |
| 7 | <5 | 56 | 7.6 | 106 | 7.2 |
| 36 | 5.2 | 31 | 7.6 | | |
| 1 | 7.4 | 29 | 7.8 | | |
| 84 | 5.1 | 22 | 7.4 | | |
| 3 | 7.7 | 49 | 7.1 | | |
| 91 | 6.0 | 54 | 7.2 | | |
| 73 | 6.5 | 52 | 7.9 | | |
| 72 | 8.0 | 55 | 5.8 | | |
| 74 | 8.3 | 38 | 7.6 | | |
| 77 | 6.1 | 94 | 7.5 | | |
| 79 | 5.7 | 88 | 7.2 | | |
| 78 | 6.4 | 83 | 6.2 | | |
| 89 | 7.4 | 9 | 6.1 | | |
| 15 | 5.8 | 99 | 6.1 | | |
| 61 | 7.6 | 42 | 7.3 | | |
| 43 | 6.9 | 40 | 8.0 | | |
| 35 | 5.7 | 39 | 7.3 | | |
| 26 | 5.5 | 53 | 7.7 | | |
| 90 | 6.8 | 95 | 7.3 | | |
| 75 | 7.8 | 103 | 5.2 | | |
| 70 | 5.9 | 92 | 7.2 | | |
| 25 | 5.8 | 93 | 7.2 | | |
| 59 | <5 | 97 | 7.6 | | |

Acceleration of Gastric Emptying and Small Intestinal Propulsion in NMRI-Mice

Male NMRI-mice weighing around 25 gram were fasted for 20 h and had free access to drinking water. Test compounds were administered to the animals by subcutaneous route 30 min before they were given a test meal by oral gavage. The test meal consisted of 0.3 ml of a chocolate nutridrink solution (1.0 kcal/ml) containing phenol red marker (5 mg/ml). Fifteen min after administration of the meal, the mice were sacrificed by $CO_2$ gas inhalation. The phenol red content remaining in the stomach (extracted from the stomach with NaOH) was determined at 557 nm in a spectrophotometer and expressed as extinction units. Small intestinal propulsion was determined as the distance traveled by the phenol red marker through the intestine and expressed as a percentage of total small intestinal length (from the pylorus to the ileo-cecal junction).

All-or-non criteria for significant ($p<0.05$) effects were defined by analysing the frequency distribution of control data: a cut-off criterion for stomach content of phenol red, below which gastric emptying was considered to be significantly accelerated, was set at 0.9 extinction units. Small intestinal propulsion was considered to be significantly accelerated when the phenol red front had progressed beyond 85% of small intestinal length. A drug effect at a given dose was considered active when ≥60% of animals tested showed a significant effect on either parameter. The lowest dose that was active for each parameter was noted as the lowest active dose (LAD). Table 12 discloses LAD values. The LAD for the reference compound GHRP-6 was 0.63 mg/kg for acceleration of gastric emptying, and 2.5 mg/kg for stimulation of small intestinal propulsion (n=3/dose).

TABLE 12

LAD values (mg/kg) for acceleration of gastric emptying and for stimulation of small intestinal propulsion

| Comp. No. | LAD (mg/kg) Gastric emptying | LAD (mg/kg) Small intestinal propulsion |
|---|---|---|
| 106 | 10 | 10 |
| 4 | >10 | >10 |
| 66 | >10 | 10 |
| 105 | 10 | >10 |
| 21 | >10 | >10 |
| 14 | 10 | >10 |
| 13 | 10 | >10 |
| 46 | 10 | 10 |
| 16 | 10 | >10 |
| 1 | 2.5 | 2.5 |
| 3 | 0.63 | 0.63 |
| 73 | >10 | 10 |
| 72 | >10 | >10 |
| 74 | >40 | >40 |
| 78 | >10 | >10 |
| 89 | >10 | >10 |
| 43 | >10 | >10 |
| 35 | >10 | >10 |
| 58 | >10 | >10 |
| 30 | 10 | >10 |
| 57 | 10 | 10 |
| 48 | >10 | >10 |
| 41 | >10 | >10 |
| 27 | >10 | >10 |
| 19 | >10 | >10 |
| 67 | >10 | >10 |
| 60 | >10 | 10 |
| 56 | 10 | >10 |
| 29 | 10 | 10 |
| 22 | >10 | >10 |
| 54 | >40 | >40 |
| 52 | >10 | >10 |
| 38 | >10 | >10 |
| 94 | 10 | 2.5 |
| 88 | >10 | >10 |
| 83 | >10 | >10 |
| 99 | 10 | >10 |
| 42 | >10 | >10 |
| 40 | >10 | >10 |
| 39 | >10 | >10 |
| 53 | >10 | >10 |
| 95 | >10 | >10 |
| 102 | >10 | >10 |
| 92 | >10 | >10 |
| 93 | >10 | 10 |
| 97 | 2.5 | 2.5 |
| 98 | 10 | 10 |
| 85 | >10 | >10 |
| 81 | >10 | >10 |
| 82 | >10 | >10 |
| 11 | >10 | >10 |
| 28 | >10 | >10 |
| 12 | >10 | >10 |
| 96 | >10 | >10 |

Acceleration of Gastric Emptying in Wild Type and GHS1A-r$^{-/-}$, KO Mice

Compound 3 or its vehicle were administered (10 mg/kg subcutaneous) to mice with a deletion of GHS1A-r (GHS1A-r$^{-/-}$, KO) or their wild type litter mates (GHS1A-r$^{+/+}$, WT) 30 minutes before administration of a phenol red containing test meal by oral gavage. 15 minutes after administration of the test meal, the meal content remaining in the stomach was determined as described above in the procedure for NMRI-mice. The stomachs of WT mice treated with compound 3 had emptied more than vehicle treated WT mice. The same treatment regimen in KO-mice revealed no difference in remaining gastric content between compound or vehicle treated KO-mice (see FIG. 1).

E. Composition Examples

"Active ingredient" (a.i.) as used throughout these examples relates to a compound of formula (I), including any stereochemically isomeric form thereof, a N-oxide thereof, a pharmaceutically acceptable salt thereof or a solvate thereof; in particular to any one of the exemplified compounds Typical examples of recipes for the formulation of the invention are as follows:

1. Tablets

| Active ingredient | 5 to 50 mg |
| --- | --- |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution.

4. Ointment

| Active ingredient | 5 to 1000 mg |
| --- | --- |
| Stearyl alcohol | 3 g |
| Lanoline | 5 g |
| White petroleum | 15 g |
| Water | ad 100 g |

The invention claimed is:

1. A method of treating a digestive disorder requiring prokinetic therapy comprising effective amount of a compound of formula

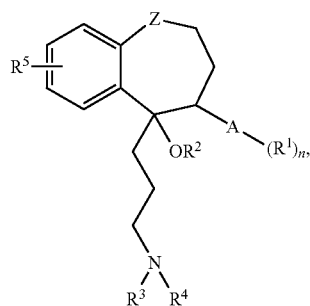

(I)

including any stereochemically isomeric form thereof, wherein

A represents phenyl, thienyl, furanyl or a 6-membered aromatic heterocycle containing 1 or 2 nitrogen atoms;

wherein said phenyl, thienyl, furanyl or 6-membered aromatic heterocycle may optionally be fused with phenyl or a 6-membered aromatic heterocycle containing 1 or 2 nitrogen atoms;

Z represents $CH_2$ or O;

$R^1$ represents halo, hydroxyl, $C_{1-4}$alkyl, $C_{1-4}$alkyloxy, polyhalo$C_{1-4}$alkyl, cyano, nitro, amino, mono or di($C_{1-4}$alkyl)amino; or in case A represents phenyl then two adjacent $R^1$ substituents may be taken together to form a radical of formula

 (a-1); or

 (a-2);

$R^2$ represents hydrogen or $C_{1-4}$alkyl;

$R^3$ and $R^4$ each independently represent hydrogen, $C_{1-6}$alkyl, $C_{1-4}$alkyloxy$C_{1-6}$alkyl or phenyl$C_{1-4}$alkyl; or $R^3$ and $R^4$ are taken together with the nitrogen to which they are attached to form a radical of formula (b-1) or (b-2)

 (b-1) or

 (b-2)

with $X_1$ representing $CH_2$ or CHOH; and $X_2$ representing $CH_2$, O or $NR^6$;

$R^5$ represents hydrogen, halo, $C_{1-4}$alkyl, $C_{1-4}$alkyloxy or trifluoromethyl;

$R^6$ represents hydrogen, $C_{1-4}$alkyl, $C_{1-4}$alkylcarbonyl, $C_{1-4}$alkyloxycarbonyl, or phenyloxycarbonyl;

n represents an integer of value 0, 1, 2, 3, 4 or 5;

a N-oxide thereof, a pharmaceutically acceptable salt thereof or a solvate thereof;

provided that the compound is other than

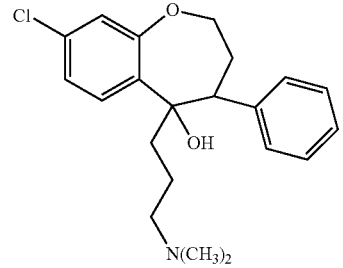 [SMILES: CN(C)CCCC1(O)c2ccc(Cl)cc2OCCC1c1ccccc1]

or a pharmaceutically acceptable salt thereof.

2. A method for treating a disease selected from the group consisting of idiopathic or diabetic gastroparesis, postoperative ileus, opioid-induced bowel dysfunction, short bowel syndrome, chronic intestinal pseudo-obstruction, emesis, constipation, delayed gastric emptying associated with wasting conditions, gastro-esophageal reflux disease (GERD), gastric ulcers, and colic comprising administering to a warm-blooded mammal suffering from said disease an effective amount of a compound of formula

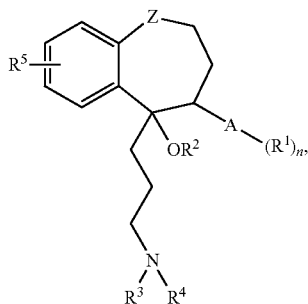
(I)

including any stereochemically isomeric form thereof, wherein

A represents phenyl, thienyl, furanyl or a 6-membered aromatic heterocycle containing 1 or 2 nitrogen atoms; wherein said phenyl, thienyl, furanyl or 6-membered aromatic heterocycle may optionally be fused with phenyl or a 6-membered aromatic heterocycle containing 1 or 2 nitrogen atoms;

Z represents $CH_2$ or O;

$R^1$ represents halo, hydroxyl, $C_{1-4}$alkyl, $C_{1-4}$alkyloxy, polyhalo$C_{1-4}$alkyl, cyano, nitro, amino, mono or di($C_{1-4}$alkyl)amino; or in case A represents phenyl then two adjacent $R^1$ substituents may be taken together to form a radical of formula

—O—$CH_2$—O— (a-1); or

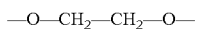
—O—$CH_2$—$CH_2$—O— (a-2);

$R^2$ represents hydrogen or $C_{1-4}$alkyl;

$R^3$ and $R^4$ each independently represent hydrogen, $C_{1-6}$alkyl, $C_{1-4}$alkyloxy$C_{1-6}$alkyl or phenyl$C_{1-4}$alkyl; or $R^3$ and $R^4$ are taken together with the nitrogen to which they are attached to form a radical of formula (b-1) or (b-2)

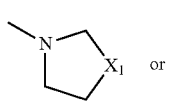
(b-1)

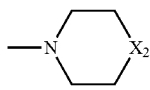
(b-2)

with $X_1$ representing $CH_2$ or CHOH; and $X_2$ representing $CH_2$, O or $NR^6$;

$R^5$ represents hydrogen, halo, $C_{1-4}$alkyl, $C_{1-4}$alkyloxy or trifluoromethyl;

$R^6$ represents hydrogen, $C_{1-4}$alkyl, $C_{1-4}$alkylcarbonyl, $C_{1-4}$alkyloxycarbonyl, or phenyloxycarbonyl;

n represents an integer of value 0, 1, 2, 3, 4 or 5;

a N-oxide thereof, a pharmaceutically acceptable salt thereof or a solvate thereof;

provided that the compound is other than

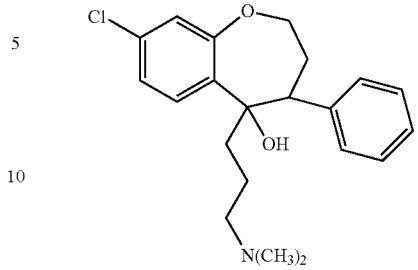

or a pharmaceutically acceptable salt thereof.

3. The method as claimed in claim 2 wherein A represents phenyl or phenyl substituted with 1, 2 or 3 $R^1$ substituents.

4. The method as claimed in claim 2 wherein A represents a radical of formula

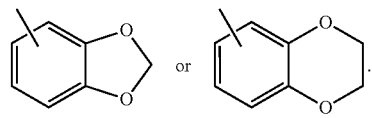

5. The method as claimed in claim 2 wherein A represents pyridyl, pyrimidinyl or quinolinyl, each of said pyridyl, pyrimidinyl or quinolinyl optionally being substituted with 1, 2 or 3 $R^1$ substituents.

6. The method as claimed in claim 2 wherein Z represents $CH_2$.

7. The method as claimed in claim 2 wherein Z represents O.

8. The method as claimed in claim 2 wherein $R^1$ represents halo, hydroxyl, $C_{1-4}$alkyl or $C_{1-4}$alkyloxy.

9. The method as claimed in claim 2 wherein $R^2$ represents hydrogen.

10. The method as claimed in claim 2 wherein $R^3$ and $R^4$ each independently represent hydrogen, $C_{1-6}$alkyl, $C_{1-4}$alkyloxy$C_{1-6}$alkyl, or phenyl$C_{1-4}$alkyl; or $R^3$ and $R^4$ are taken together with the nitrogen to which they are attached to form a radical of formula (b-1) or (b-2)

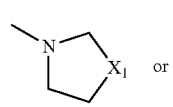
(b-1)

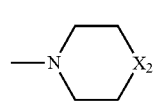
(b-2)

with $X_1$ representing $CH_2$ or CHOH; and $X_2$ representing $CH_2$.

11. The method as claimed in claim 10 wherein $R^3$ and $R^4$ each independently represent hydrogen, $C_{1-6}$alkyl, $C_{1-4}$alkyloxy$C_{1-6}$alkyl, or phenyl$C_{1-4}$alkyl; or $R^3$ and $R^4$ are taken together with the nitrogen to which they are attached to form a radical of formula (b-1)

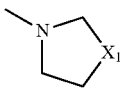 (b-1)

with $X_1$ representing $CH_2$ or CHOH.

12. The method as claimed in claim 2 wherein n represents an integer of value 1 or 2.

13. The method as claimed in claim 2 wherein n is 0.

14. The method as claimed in claim 2 wherein A represents phenyl, 1,3-benzodioxolyl, 2,3-dihydro-1,4-benzodioxinyl, pyridyl, pyrimidinyl, quinolinyl; each of said rings optionally being substituted with 1 or 2 substituents each independently selected from halo, hydroxyl, $C_{1-4}$alkyl or $C_{1-4}$alkyloxy; $R^3$ and $R^4$ each independently represent hydrogen, $C_{1-4}$alkyl, $C_{1-4}$alkyloxy$C_{1-4}$alkyl, phenyl$C_{1-4}$alkyl; or $R^3$ and $R^4$ are taken together with the nitrogen to which they are attached to form pyrrolidinyl optionally substituted in position 3 with hydroxyl; piperidinyl; morpholinyl; piperazinyl optionally substituted with $C_{1-4}$alkyl or $C_{1-4}$alkylcarbonyl; $R^2$ represents hydrogen or methyl.

15. The method as claimed in claim 2 wherein the substituents on the cycloheptane or oxepine ring have a cis configuration.

16. The method as claimed in claim 2 wherein the compound is an enatiomeric pure form.

17. The method as claimed in claim 2 wherein the compound is selected from (±) cis-6-(4-Chloro-3-methoxy-phenyl)-5-(3-diethylamino-propyl)-6,7,8,9-tetrahydro-5H-benzocyclohepten-5-ol oxalate;

(±) cis-6-(3-Chloro-phenyl)-5-(3-diethylamino-propyl)-6,7,8,9-tetrahydro-5H-benzocyclohepten-5-ol oxalate;

(±) cis-4-(4-Chloro-3-methoxy-phenyl)-5-(3-diethylamino-propyl)-2,3,4,5-tetrahydro-benzo[b]oxepin-5-ol oxalate;

(±) cis-6-(3-Chloro-phenyl)-5-(3-dimethylamino-propyl)-6,7,8,9-tetrahydro-5H-benzocyclohepten-5-ol oxalate;

(±) cis-6-(4-Chloro-3-methoxy-phenyl)-5-(3-dimethylamino-propyl)-6,7,8,9-tetrahydro-5H-benzocyclohepten-5-ol;

(±) cis-6-(4-Chloro-phenyl)-5-(3-dimethylamino-propyl)-6,7,8,9-tetrahydro-5H-benzocyclohepten-5-ol oxalate;

(±) cis-5-(3-Dimethylamino-propyl)-6-(3-methoxy-phenyl)-6,7,8,9-tetrahydro-5H-benzocyclohepten-5-ol oxalate;

(±) cis-5-(3-Dimethylamino-propyl)-6-(4-fluoro-phenyl)-6,7,8,9-tetrahydro-5H-benzocyclohepten-5-ol oxalate;

(±) cis-5-(3-Dimethylamino-propyl)-6-phenyl-6,7,8,9-tetrahydro-5H-benzocyclohepten-5-ol oxalate;

(±) cis-6-(4-Chloro-3-methoxy-phenyl)-5-{3-[(2-methoxy-ethyl)-methyl-amino]-propyl}-6,7,8,9-tetrahydro-5H-benzocyclohepten-5-ol oxalate;

(±) cis-5-(3-Dimethylamino-propyl)-6-p-tolyl-6,7,8,9-tetrahydro-5H-benzocyclohepten-5-ol oxalate;

(±) cis-5-(3-Diethylamino-propyl)-6-(4-fluoro-phenyl)-6,7,8,9-tetrahydro-5H-benzocyclohepten-5-ol oxalate;

(±) cis-6-(2,4-Difluoro-phenyl)-5-(3-dimethylamino-propyl)-6,7,8,9-tetrahydro-5H-benzocyclohepten-5-ol oxalate;

(±) cis-4-(4-Chloro-3-methoxy-phenyl)-5-(3-dimethylamino-propyl)-2,3,4,5-tetrahydro-benzo[b]oxepin-5-ol oxalate;

(±) cis-5-(3-Diethylamino-propyl)-6-p-tolyl-6,7,8,9-tetrahydro-5H-benzocyclohepten-5-ol oxalate;

(±) cis-5-(3-Diethylamino-propyl)-6-(3-methoxy-phenyl)-6,7,8,9-tetrahydro-5H-benzocyclohepten-5-ol hydrochloride;

(±) cis-6-(4-Bromo-phenyl)-5-(3-dimethylamino-propyl)-6,7,8,9-tetrahydro-5H-benzocyclohepten-5-ol oxalate;

(±) cis-6-(5-Chloro-pyridin-3-yl)-5-(3-dimethylamino-propyl)-6,7,8,9-tetrahydro-5H-benzocyclohepten-5-ol hydrochloride;

(±) cis-5-(3-Dimethylamino-propyl)-6-quinolin-3-yl-6,7,8,9-tetrahydro-5H-benzocyclohepten-5-ol;

(±) cis-5-(3-Dimethylamino-propyl)-6-(6-methyl-pyridin-3-yl)-6,7,8,9-tetrahydro-5H-benzocyclohepten-5-ol hydrochloride.

* * * * *